United States Patent [19]

Brocchini et al.

[11] Patent Number: 5,891,877
[45] Date of Patent: Apr. 6, 1999

[54] PHARMACEUTICAL COMPOUNDS

[75] Inventors: Stephen James Brocchini, Highland Park, N.J.; Justin Stephen Bryans, Slough, United Kingdom; Adrian John Folkes, Slough, United Kingdom; Christopher John Latham, Slough, United Kingdom; Julie Elizabeth Brumwell, Slough, United Kingdom

[73] Assignee: Xenova Limited, United Kingdom

[21] Appl. No.: 693,172

[22] PCT Filed: Feb. 14, 1995

[86] PCT No.: PCT/GB95/00302

§ 371 Date: Sep. 25, 1996

§ 102(e) Date: Sep. 25, 1996

[87] PCT Pub. No.: WO95/21832

PCT Pub. Date: Aug. 17, 1995

[51] Int. Cl.$^6$ .................. A61K 31/495; A61K 31/535; C07D 241/08; C07D 401/06
[52] U.S. Cl. .................. 514/235.8; 514/252; 514/253; 514/255; 544/121; 544/35.7; 544/360; 544/363; 544/364; 544/365; 544/370; 544/372; 544/373; 544/377; 544/379; 544/385
[58] Field of Search .................. 544/385, 370, 544/373, 360, 379, 372, 377, 363, 357, 121; 514/252, 253, 235.8, 255, 364, 365

[56] References Cited

U.S. PATENT DOCUMENTS 5,750,530  5/1998  Bryans et al. .................. 514/255

FOREIGN PATENT DOCUMENTS

C-621862  10/1935  Germany.
A-9404512  3/1994  WIPO.

OTHER PUBLICATIONS

Yokoi et al, Journal of Antibiotics, vol. XLI, pp. 494–501, (1988).
Wu et al, *Chemical Abstracts*, vol. 113, No. 17408 (1990).
Drug Evalvations by American Medical Association, pp. 745–746, (1993).
Chemical Abstracts, vol. 65, 1966 16969—38–Heterocyclic Compounds 2,5–dioxopipeazines. II Reaction of 2,5–di-opiperazine with aldehydes and nitroso compounds, Augustin et al.
The Lancet, Jul. 1987 pp. 3–8 Hamsten et al Plasminogen Activator Inhibitor in Plasma: Risk Factor for Recurrent Myocardial Infarction, Hansten et al.
Circulation vol. 96 No. 3 Aug. 1997 pp. 916–921 Friederick at al Novel Low–Molecular–Weight Inhibitor of PA–1 etc.
Thrombosis and Haemostasis 1996 pp. 808–815 Charlton et al Evaluation of a Low Molecular Weight etc.
Seminars in Thrombosis and Hemostasis vol. 18 No. 1 1992 pp. 67–80 Krishnamurti et al Plasmiogen Activator INhibitor Type 1: Biochemistry and Evidence for Modulation of Fibrinolysis in Vivo.
Chemical Abstracts, vol. 97, No. 6, 1982, Columbus, OH, U.S. abstract No. 40323s p. 70.

*Primary Examiner*—Emily Bernhardt
*Attorney, Agent, or Firm*—Nixon & Vanderhye

[57] ABSTRACT

Diketopiperazines of the formula (A)

$$R_1 \text{—} \underset{HN}{\overset{O}{\underset{\|}{\text{C}}}} \text{—} NH \text{—} \underset{O}{\overset{}{\text{C}}} \text{—} R_2$$

where one or both of $R_1$ and $R_2$, which are different, are chosen from X and a phenyl group substituted by X, C(O)X, OC(O)CH$_2$X, OCH$_2$CH$_2$X, CH$_2$X, CONH(CH$_2$)$_n$X, O(CH$_2$)$_n$CH(OH)(CH$_2$)$_n$X $$-\text{C(O)NH} \text{—} \left(\text{—}\bigcirc\text{—}\right)_n \text{—} (\text{CH}_2)_m \text{—} X$$

and, where appropriate, the other of $R_1$ and $R_2$ is a phenyl group optionally substituted by one or more groups selected from halogen, nitro, methoxy, NHC(O)R$_{12}$, CO$_2$H, O(CH$_2$)$_n$N(R$_{12}$R$_{13}$), C$_1$–C$_4$ alkyl and (CH$_2$)$_n$C(O)OR$_{12}$; X is a five- or six-membered heterocyclic ring selected from the group consisting of pyridyl, imidazolyl, furyl, pyrrolyl, pyrrolidinyl, thienyl, piperazinyl, piperidinyl, morpholinyl, quinolyl, isoquinotyl and indolyl, the heteroatom(s) of the said heterocyclic ring, when nitrogen, being optionally substituted by hydrogen, methyl, oxygen, tertiary-butyloxycarbonyl, or SO$_2$Me, the heterocyclic ring being optionally substituted by halogen [hydrogen], methyl, MeS, phenyl, O(CH$_2$)$_n$N(R$_{12}$R$_{13}$) or optionally containing one or more carbonyl groups and being optionally fused to a benzene ring; Y is O or S; R$_{12}$ and R$_{13}$, which may be the same or different, are hydrogen or C$_1$–C$_6$ alkyl; and n is 0 or an integer having the value 1, 2, 3 or 4; a pharmaceutically acceptable salts or esters having activity as inhibitors of plasminogen activator inhibitor.

18 Claims, No Drawings

PHARMACEUTICAL COMPOUNDS

The present invention relates to compounds useful as inhibitors of plasminogen activator inhibitor (PAI), to their preparation and to pharmaceutical and veterinary compositions containing them.

Plasminogen activators (Pas) are serine proteases which control the activation of the zymogen, plasminogen, to the active enzyme plasmin. Plasmin is important in a number of physiological and pathological processes including fibrinolysis, tissue remodelling, tumour growth and metastasis. The glycoprotein plasminogen activator inhibitor (PAI) is an endogenous fast-acting inhibitor of PA activity. PAI is a member of the serpin family and is synthesised by a variety of cells including endothelial cells. An imbalance between PAs and PAI contributes to a number of pathological conditions including haemostasis, inflammation, tumour growth and metastasis.

The present invention provides a diketopiperazine of formula (A):

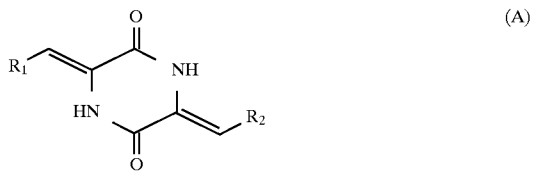

wherein one or both of $R_1$ and $R_2$, which may be the same or different, is:

(I) X, or a phenyl group which is substituted by X, C(O)X, OC(O)CH$_2$X, OCH$_2$CH$_2$X, CH$_2$X, CONH(CH$_2$)$_n$X, O(CH$_2$)$_n$CH(OH)(CH$_2$)$_n$X or

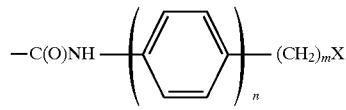

or which is fused to a group X;

(II) a phenyl group substituted by CH$_2$NR$_{12}$R$_{13}$, OC(O)(CH$_2$)$_n$Z, CH(OR$_{12}$)(OR$_{13}$), (CH$_2$)$_n$NR$_{14}$C(O)(CH$_2$)$_m$NR$_{12}$R$_{13}$, —CH$_2$NR$_{12}$—(CH$_2$)$_n$NR$_{15}$R$_{16}$ or O(CH$_2$)$_n$CH(OH)(CH$_2$)$_n$N(R$_{12}$R$_{13}$);

(III) a group CH=C(W)V; or (IV) a cyclohexyl group; and where appropriate, the other of $R_1$ and $R_2$ is a phenyl group optionally substituted by one or more groups independently selected from halogen, nitro, methoxy, NHC(O)R$_{12}$, CO$_2$H, O(CH$_2$)$_n$N(R$_{12}$R$_{13}$), CH$_2$Y(CH$_2$)$_n$N(R$_{12}$R$_{13}$), C$_1$–C$_4$ alkyl and (CH$_2$)$_n$C(O)OR$_{12}$;

X is a naphthyl group or a five- or six-membered saturated or unsaturated heterocyclic group containing one or more heteroatoms, which heteroatoms may be the same or different and are independently selected from O, N and S; the heteroatom(s) when nitrogen being optionally substituted by hydrogen, methyl, oxygen, tertiary-butyloxycarbonyl, —(CH$_2$)$_n$CH$_2$OH or SO$_2$Me; the heterocyclic ring being optionally substituted by halogen, Me, MeS, phenyl, O(CH$_2$)$_n$NR$_{12}$R$_{13}$, —N(R$_{12}$) (CH$_2$)$_n$N(R$_{12}$R$_{13}$), —(CH$_2$)$_n$N(R$_{12}$R$_{13}$) or —O(CH$_2$)$_n$O(CH$_2$)$_n$N(R$_{12}$R$_{13}$), or the heterocyclic ring optionally containing one or more carbonyl groups and being optionally fused to a benzene ring, which benzene ring is optionally substituted by 1 or 2 C$_1$–C$_6$ alkoxy groups;

Y is O or S;

Z is a C$_3$–C$_6$ cycloalkyl group;

R$_{12}$, R$_{13}$ and R$_{14}$, which may be the same or different, are hydrogen or C$_1$–C$_6$ alkyl;

R$_{15}$ and R$_{16}$, which may be the same or different, are hydrogen or C$_1$–C$_6$ alkyl, or R$_{15}$ and R$_{16}$ form, together with the nitrogen atom to which they are attached, a 5- or 6-membered heterocyclic group;

W is hydrogen or a phenyl group;

V is a phenyl group optionally substituted by one or more groups independently selected from nitro, alkoxy, O(CH$_2$)$_n$NR$_{12}$R$_{13}$, and NR$_{12}$R$_{13}$; and m and n are each, independently, 0 or an integer having tie value 1, 2, 3 or 4;

or a pharmaceutically acceptable salt or ester thereof.

A C$_1$–C$_6$ alkyl group is, for example, a C$_1$–C$_4$ alkyl group, such as a methyl, ethyl, propyl, i-propyl, n-butyl, sec-butyl or tert-butyl group.

A halogen may be F, Cl, Br or I.

In compounds of formula A free rotation may occur at room temperature about the single bonds connecting substituents $R_1$ and $R_2$ to the double bonds at positions 3 and 6 of the piperazine-2,5-dione ring.

In one embodiment at least one of $R_1$ and $R_2$, which may be the same or different, is chosen from a naphthyl group, X, a phenyl group substituted by X, C(O)X, OC(O)CH$_2$X, OCH$_2$CH$_2$X, or CH$_2$X and a phenyl group which is fused to a group X; wherein X is a five- or six-membered saturated or unsaturated heterocyclic group containing one or two heteroatoms, which heteroatoms may be the same or different and are independently selected from O, N and S, the heteroatom(s) when nitrogen being optionally substituted by hydrogen, methyl, oxygen, tertiary-butyloxycarbonyl, —(CH$_2$)$_n$CH$_2$OH or SO$_2$Me, the heterocyclic ring being optionally substituted by hydrogen, halogen, methyl, MeS, phenyl, O(CH$_2$)$_n$NR$_{12}$R$_{13}$, O(CH$_2$)$_n$N(R$_{12}$R$_{13}$) or —O(CH$_2$)$_n$O(CH$_2$)$_n$N(R$_{12}$R$_{13}$); the heterocyclic ring optionally containing one or more carbonyl groups, and being optionally fused to a benzene ring; and the other of $R_1$ and $R_2$ is a phenyl group optionally substituted at the 2, 3 or 4-position by CH$_2$NR$_{12}$R$_{13}$, (CH$_2$)$_n$NR$_{14}$C(O)(CH$_2$)$_m$NR$_{12}$R$_{13}$, halogen, nitro, —NHC(O)R$_{12}$, —O(CH$_2$)$_n$N(R$_{12}$R$_{13}$) or —CH$_2$Y(CH$_2$)$_n$N(R$_{12}$R$_{13}$) wherein Y is O or S. In a particularly preferred series of compounds the said other of $R_1$ and $R_2$ is a phenyl group substituted at the 4-position by —O(CH$_2$)$_n$N(R$_{12}$R$_{13}$), —CH$_2$Y(CH$_2$)$_n$N(R$_{12}$R$_{13}$) or —(CH$_2$)$_n$NR$_{14}$C(O) (CH$_2$)$_m$NR$_{12}$R$_{13}$.

In a further embodiment one of $R_1$ and $R_2$ is X, a phenyl group substituted by X, —CH$_2$X, —OCH$_2$CH$_2$X, O(CH$_2$)$_n$CH(OH)CH$_2$X or

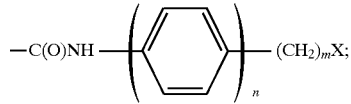

wherein X is a 5 or 6-membered saturated or unsaturated heterocyclic group as defined above which is optionally substituted and optionally fused to a benzene ring, for instance a pyridyl, imidazolyl, furyl, pyrrolyl, pyrrolidinyl, thienyl, piperazinyl, piperidinyl, morpholinyl, quinolyl, isoquinolyl or indolyl group; and the other of $R_1$ and $R_2$ is a phenyl group optionally substituted at the 4-position by —O(CH$_2$)$_n$N(R$_{12}$R$_{13}$) —CH$_2$Y(CH$_2$)$_n$N(R$_{12}$R$_{13}$) or —(CH$_2$)$_n$NR$_{14}$C(O)(CH$_2$)$_m$NR$_{12}$R$_{13}$. In this embodiment it is particularly preferred for X to be a furyl, imidazolyl, pyrrolyl, thienyl, morpholinyl, piperidinyl or isoquinolyl group.

In a further embodiment, $R_{12}$ and $R_{13}$, which may be the same or different, are hydrogen or $C_1$–$C_3$ alkyl and n is an integer of value 1 or 2.

In a yet further embodiment one of $R_1$ and $R_2$ is a phenyl group which is substituted by X, CO(X), OCO(O)CH$_2$X, OCH$_2$CH$_2$X, CH$_2$X or which is fused to a group X, wherein X is a five- or six-membered heterocyclic ring containing one or two heteroatoms which may be the same or different, independently selected from O, N and S, the heteroatom(s) when nitrogen being optionally substituted by methyl, and the heterocyclic ring being optionally fused to a benzene ring.

In another embodiment one of $R_1$ and $R_2$ is a phenyl group substituted by CH$_2$NR$_{12}$R$_{13}$, OC(O)(CH$_2$)$_n$Z, CH(OR$_{12}$)(OR$_{13}$), (CH$_2$)$_n$NR$_{14}$C(O)(CH$_2$)$_m$N(R$_{12}$R$_{13}$); wherein $R_{12}$, $R_{13}$ and $R_{14}$, which may be the same or different, are independently selected from hydrogen or $C_1$–$C_3$ alkyl; Z is a $C_5$ or $C_6$ cycloalkyl group; and m and n are, independently, integers having the values 1, 2 or 3.

In a further embodiment $R_{12}$, $R_{13}$ and $R_{14}$, which may be the same or different, are independently selected from hydrogen and $C_1$–$C_2$ alkyl; Z is a cyclopentyl group; and m and n are, independently, integers having the values of 1 or 2.

In a yet further embodiment one of $R_1$ and $R_2$ is a phenyl group optionally substituted by one or more groups independently selected from chloro, nitro, methoxy, NHCOR$_{12}$, CO$_2$H and O(CH$_2$)$_n$NR$_{12}$R$_{13}$; $R_{12}$ and $R_{13}$, which may be the same or different, are independently selected from hydrogen or methyl and n is an integer having the value 1 or 2.

In another embodiment one of $R_1$ and $R_2$ is a group CH=C(W)V, W is a phenyl group optionally substituted by one of more groups independently selected from nitro, methoxy and O(CH$_2$)$_n$NMe$_2$ and n is an integer having the value 1, 2,3 or 4.

In a further embodiment n is 1 or 2.

In a yet further embodiment one of $R_1$ and $R_2$ is a phenyl group optionally substituted by NHAc or methoxy.

In another embodiment one of $R_1$ and $R_2$ is cyclohexyl and the other is a phenyl group optionally substituted by NHC(O)R$_{12}$.

In a further embodiment one of $R_1$ and $R_2$ is cyclohexyl and the other is a phenyl group optionally substituted by NHC(O)Me.

In a further embodiment $R_3$ is $C_1$–$C_2$ alkyl or (CH$_2$)$_n$C(O)OR$_{12}$; $R_{12}$ is hydrogen or $C_1$–$C_2$ alkyl and n is an integer of value 1 or 2.

In a yet further embodiment $R_3$ is methyl or CH$_2$C(O)OR$_{12}$ and $R_{12}$ is hydrogen or methyl.

Certain diketopiperazines have been disclosed as having utility as bioactive agents. Yokoi et al in J. Antibiotics vol XLI No. 4, pp 494–501 (1988) describe structure-cytotoxicity relationship studies on a series of diketopiperazines related to neihumicin, a compound obtained from the micro-organism *Micromonospora neihuensis*. Kamei et al in J. Antibiotics vol XLIII No. 8, 1018–1020 disclose that two diketopiperazines, designated piperafizines A and B, have utility as potentiators of the cytotoxicity of vincristine.

Examples of specific compounds of formula A are as follows. The compound numbering is adhered to in the rest of the specification:

1926 (3Z,6Z)-3-Benzylidene-6-(4-imidazolyl)methylene-2,5-piperazinedione.

1930 (3Z,6Z)-3-Benzylidene-6-(4-(1-imidazolyl)benzylidene-2,5-piperazinedione.

1929 (3Z,6Z)-3-Benzylidene-6-(4-(1-imidazolylmethyl)benzylidene)-2,5-piperazinedione.

1959 (3Z,6Z)-3,Benzylidene-6-(4-(2-dimethylaminoethoxy)-3-methoxybenzylidene)-2,5-piperazinedione hydrochloride.

1927 (3Z,6Z)-3-Benzylidene-6-(4-(5-methylimidazolyl))methylene-2,5-piperazinedione.

1921 (3Z,6Z)-3-Benzylidene-6-(4-dimethylaminocinnamylidene)-2,5-piperazinedione.

1976 (3Z,6Z)-3-(4-(3-Dimethylaminopropoxy)benzylidene)-6-(4-(1-imidazolyl)benzylidene-2,5-piperazinedione.

1910 (3Z,6Z)-3-Benzylidene-6-(4-(2-imidazolylethoxy)benzylidene)-2,5-piperazinedione.

1923 (3Z,6Z)-3-Benzylidene-6-(4-nitrocinnamylidene-2,5-piperazinedione.

1657 (3Z,6Z)-3-(4-Aminomethylbenzylidene)-6-(4-methoxybenzylidene)-2,5-piperazinedione.

1693 (3Z,6Z)-3-(1-methanesulfonyl-3-indolyl)methylene-6-(4-methoxybenzylidene)-2,5-piperazinedione.

1886 (3Z,6Z)-3-(4-Methoxybenzylidene)-6-(4-phthalimidoacetoxybenzylidene)-2,5-piperazinedione.

1922 (3Z,6Z)-3-Benzylidene-6-(γ-phenylcinnamylidene)-2,5-piperazinedione.

1618 (3Z,6Z)-3-(1-tert-butoxycarbonyl-3-indolyl)methylene-6-(2-thenylidene)-2,5-piperazinedione.

1560 (3Z,6Z)-3-(2,6-Dichlorobenzylidene)-6-(1-tert-butoxycarbonyl-3-indolyl)methylene-2,5-piperazinedione.

1950(3Z,6Z)-3-Benzylidene-6-(4-(2-dimethylaminoethoxy)-3-methoxycinnamylidene)-2,5-piperazinedione.

1975 (3Z,6Z)-3-(4-(3-Dimethylaminopropoxy)benzylidene)- 6-(4-(1-imidazolylmethyl)benzylidene)-2,5-piperazinedione.

1983 (3Z,6Z)-3-Benzylidene-6-(4-N-methyl-N-(4-(N-methylpiperidinyl))aminomethylbenzylidene-2,5-piperazinedione.

1509 (3Z,6Z)-3-Benzylidene-6-(3-indolylmethylene)-2,5-piperazinedione.

1542 (3Z,6Z)-3-(2,6-Dichlorobenzylidene)-6-(3-furylmethylene)-2,5-piperazinedione.

1545 (3Z,6Z)-3-(3-Indolylmethylene)-6-(4-methoxybenzylidene)-2,5-piperazinedione.

1507 (3Z,6Z)-3-(4-Methoxybenzylidene)-6-(2-(1-tertbutoxycarbonyl)pyrrolyl)methylene- 2,5-piperazinedione.

1506 (3Z,6Z)-3-(4-Methoxybenzylidene)-6-(3-(1-tert-butoxycarbonyl)indolyl)methylene-2,5-piperazinedione.

1471 (3Z,6Z)-3-Benzylidene-6-(3-(1-tert-butoxycarbonyl)indolyl)methylene-2,5-piperazinedione.

1474 (3Z,6Z)-3-(4-Methoxybenzylidene)-6-(2-thienylmethylene)-2,5-piperazinedione.

1476 (3Z,6Z)-3-(4-Methoxybenzylidene)-6-(3-furylmethylene)-2,5-piperazinedione.

1672 (3Z,6Z)-3-(Acetamidobenzylidene)-6-cyclohexylmethylene-2,5-piperazinedione.

1676 (3Z,6Z)-3-(4-Acetamidobenzylidene)-6-cinnamylidene-2,5-piperazinedione.

1891 (3Z,6Z)-3-Benzylidene-6-(diethoxymethylbenzylidene)-2,5-piperazinedione.

1982 (3Z,6Z)-3-Benzylidene-6-(4-(N-methyl-N-(2-dimethylaminoethyl)aminomethylbenzylidene-2,5-piperazinedione hydrochloride.

1884 (3Z,6Z)-3-Benzylidene-6-cyclohexylmethylene-2,5-piperazinedione.

1845 (3Z,6Z)-3-(4-Acetamidobenzylidene)-6-(3,4-methylenedioxybenzylidene)-2,5-piperazinedione.

1950 (3Z,6Z)-3-benzylidene-6-(4-(2-dimethylaminoethoxy)-3-methoxycinnamylidene)-2,5-piperazinedione.

1718 (3Z,6Z)-3-(2-Indolylmethylene)-6-(4-methoxybenzylidene)-2,5-piperazinedione.
1808 (3Z,6Z)-3-Benzylidene-6-(3,4-methylenedioxybenzylidene)-2,5-piperazinedione.
1809 (3Z,6Z)-3-(4-Methoxybenzylidene)-6-(3,4-methylenedioxybenzylidene)-2,5-piperazinedione.
1470 (3Z,6Z)-3-Benzylidene-6-(2-(1-tertbutoxycarbonyl)pyrrolyl)methylene-2,5-piperazinedione.
5023 (3Z,6Z)-3-(4-Dimethylaminomethylbenzylidene)-6-(4-(3-dimethylaminopropoxy)benzylidene-2,5-piperazinedione.
5026 (3Z,6Z)-3-(4-(3-Dimethylaminopropoxy)benzylidene)-6-(4-(1-imidazolyl)methylbenzylidene)-2,5-piperazinedione.
5030 (3Z,6Z)-3-(4-(3-Dimethylaminopropoxy)benzylidene)-6-(4-(1-imidazolyl)benzylidene)-2,5-piperazinedione.
5367 (2-(4-((3Z,6Z)-6-(4-(3-Dimethylaminopropoxy)benzylidene)-2,5-dioxo-3-piperazinylidene)methylbenzoyl)-1,2,3,4-tetrahydroisoquinoline.
5386 N-(2-(1,2,3,4-Tetrahydro-2-isoquinolyl)ethyl)-4-((3Z,6Z)-6-(4-(3-dimethylaminopropoxy)benzylidene)-2,5-dioxo-3-piperazinylidene)methylbenzamide.
5397 N-(4-(1,2,3,4-Tetrahydro-2-isoquinolyl)butyl)-4-((3Z,6Z)-6-(4-(3-dimethylaminopropoxy)benzylidene)-2,5-dioxo-3-piperazinylidene)methylbenzamide.
5027 (3Z,6Z)-6-(4-(3-Dimethylaminopropoxy)benzylidene-3-(4-pyridylmethylene)-2,5-piperazinedione.
5028 (3Z,6Z)-6-(4-(3-Dimethylaminopropoxy)benzylidene)-3-(3-pyridylmethylene)-2,5-piperazinedione.
5041 (3Z,6Z)-6-(4-(3-Dimethylaminopropoxy)benzylidene)-3-furfurylidene-2,5-piperazinedione.
5042 (3Z,6Z)-6-(4-(3-Dimethylaminopropoxy)benzylidene)-3-(3-Thenylidene)-2,5-piperazinedione.
5046 (3Z,6Z)-6-(4-(3-Dimethylaminopropoxy)benzylidene)-3-(2-Thenylidene)-2,5-piperazinedione.
5052 (3Z,6Z)-6-(4-(3-Dimethylaminopropoxy)benzylidene)-3-(3-Furylmethylene)-2,5-piperazinedione.
5188 (3Z,6Z)-6-(4-(3-Dimethylaminopropoxy)benzylidene)-3-(2-Naphthylmethylene)-2,5-piperazinedione.
5200 (3Z,6Z)-6-(4-(3-Dimethylaminopropoxy)benzylidene)-3-(1-Naphthylmethylene)-2,5-piperazinedione.
5032 (3Z,6Z)-6-Benzylidene-3-(4-(3-dimethylamino-2-hydroxypropoxy)benzylidene)-2,5-piperazinedione.
5040 (3Z,6Z)-6-Benzylidene-3-(4-(2-hydroxy-3-morpholinopropoxy)benzylidene)-2,5-piperazinedione.
5057 (3Z,6Z)-6-Benzylidene-3-(4-(2-hydroxy-3-(1-imidazolyl)propoxy)benzylidene)-2,5-piperazinedione.
5043 (3Z,6Z)-6-Benzylidene-3-(4-(2-hydroxy-3-(4-(2-hydroxyethyl)-1-piperazinyl)propoxy)benzylidene)-2,5-piperazinedione.
5062 (3Z,6Z)-6-(4-(2-Dimethylaminoethoxy)benzylidene)-3-(3-furylmethylene)-2,5-piperazinedione.
5071 (3Z,6Z)-6-(4-(2-Dimethylaminoethoxy)benzylidene)-3-(3-thenylidene)-2,5-piperazinedione.
5072 (3Z,6Z)-6-(4-(2-Dimethylaminoethoxy)benzylidene)-3-(5-methylthio-2-thenylidene)-2,5-piperazinedione.
5054 (3Z,6Z)-6-Benzylidene-3-(4-(2-morpholinoethoxy)benzylidene)- 2,5-piperazinedione.
5055 (3Z,6Z)-6-Benzylidene-3-(4-(2-(1-imidazolyl)ethoxy)benzylidene)2,5-piperazinedione.
5053 (3Z,6Z)-6-Benzylidene-3-(4-(2-(1-pyrrolidinyl)ethoxy)benzylidene)2,5-piperazinedione.
5069 (3Z,6Z)-6-(4-(2-Dimethylaminoethoxymethyl)benzylidene)-3-(3-thenylidene)-2,5-piperazinedione.
5077 (3Z,6Z)-6-(4-(2-Dimethylaminoethoxymethyl)benzylidene)-3-(3-furylmethylene)-2,5-piperazinedione.
5074 (3Z,6Z)-6-(4-Dimethylaminoacetamidomethyl benzylidene)-3-(3-thenylidene)-2,5-piperazinedione.
5079 (3Z,6Z)-3-(2-Bromobenzylidene)-6-(4-dimethylaminoacetamidomethylbenzylidene)-2,5-piperazinedione.
5081 (3Z,6Z)-6-(4-Dimethylaminoacetamidomethylbenzylidene)-3-(3-furylmethylene)-2,5-piperazinedione.
5061 (3Z,6Z)-6-Benzylidene-3-(4-dimethylaminoacetamidomethylbenzylidene)-2,5-piperazinedione.
5073 (3Z,6Z)-6-(4-(2-Dimethylaminoethylthiomethyl)benzylidene)-3-(3-furylmethylene)-2,5-piperazinedione.
5078 (3Z,6Z)-6-(4-(2-Dimethylaminoethylthiomethyl)benzylidene)-3-(3-thenylidene)-2,5-piperazinedione.
1912 (3Z,6Z)-6-Benzylidene-3-(4-dimethylaminoacetamidoaminomethylbenzylidene)- 2,5-piperazinedione.
5324 (3Z,6Z)-6-Benzylidene-3-(5-(2-dimethylaminoethoxy)-2-thienylmethylene)-2,5-piperazinedione.
5327 (3Z,6Z)-6-Benzylidene-3-(4-(2-dimethylaminoethoxy)-2-thienylmethylene)-2,5-piperazinedione.
5335 (3Z,6Z)-6-Benzylidene-3-(5-(2-dimethylaminoethyl)-2-thienylmethylene)-2,5-piperazinedione.
5388 (3Z,6Z)-6-Benzylidene-3-(5-(2-(2-dimethylaminoethoxy)ethoxy)-2-thienylmethylene)-2,5-piperazinedione.
5389 (3Z,6Z)-6-Benzylidene-3-(5-(6-dimethylaminohexyloxy)-2-thienylmethylene)-2,5-piperazinedione.
5299 (3Z,6Z)-6-Benzylidene-3-(5-(2-dimethylaminoethyl)methylamino-2-thienylmethylene)-2,5-piperazinedione.
5075 (3Z,6Z)-3-(2,5-Dichloro-3-thenylidene)-6-benzylidene-2,5-piperazinedione.
5371 N-(4-(1,2,3,4-Tetrahydro-2-isoquinolyl)butyl)-4-((3Z,6Z)-6-benzylidene-2,5-dioxo-3-piperazinylidene)methylbenzamide.
5391 N-(2-(1,2,3,4-Tetrahydro-2-isoquinolyl)ethyl)-4-((3Z,6Z)-6-benzylidene-2,5-dioxo-3-piperazinylidene)methylbenzamide.
5394 N-(3-(1,2,3,4-Tetrahydro-2-isoquinolyl)propyl)-4-((3Z,6Z)-6-benzylidene-2,5-dioxo-3-piperazinylidene)methylbenzamide.
5393 N-(4-(2-(1,2,3,4-Tetrahydro-2-isoquinolyl)ethyl)phenyl- 4-((3Z,6Z)-6-benzylidene-2,5-dioxo-3-piperazinylidene)methylbenzamide.
5402 N-(4-(2-(1,2,3,4-Tetrahydro-2-isoquinolyl)ethyl)phenyl)-4-((3Z,6Z)-2,5-dioxo-6-(4-nitrobenzylidene)-3-piperazinylidene)methylbenzamide.

Compounds of formula A, may be prepared by a process which comprises either (i) condensing compound of formula (I)

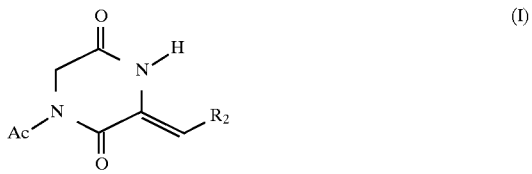

wherein $R_2$ is as defined above and is optionally protected, with a compound of formula (II):

$R_1$—CHO (II)

wherein $R_1$ is as defined above and is optionally protected, in the presence of a base in an organic solvent; or (ii) condensing a compound of formula (I'):

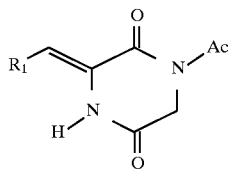

wherein $R_1$ is as defined above and is optionally protected, with a compound of formula (III):

$R_2$—CHO (III)

wherein $R_2$ is as defined above and is optionally protected, in the presence of a base in an organic solvent; and, in either case (i) or (ii), if required, removing optionally present protecting groups and/or, if desired, converting one compound of formula A into another compound of formula A, and/or, if desired, converting a compound of formula A into a pharmaceutically acceptable salt or ester thereof, and/or, if desired, converting a salt or ester into a free compound, and/or, if desired, separating a mixture of isomers of compounds of formula A into the single isomers.

A compound of formula A produced directly by the condensation reaction between (I) and (II) or (I') and (III) may be modified, if desired, by converting $R_1$ into a different $R_1$ group. These optional conversions may be carried out by methods known in themselves. For example, a compound of formula A in which $R_1$ comprises an ester group may be converted to a compound of formula A wherein the corresponding substituent is a free —COOH or OH group, by acid or alkaline hydrolysis at a suitable temperature, for example from ambient temperature to 100° C.

A compound of formula A in which either or both of $R_1$ and $R_2$ includes an —OH group may be converted into a compound of formula A wherein the corresponding substituent is esterified, for example by treating with a suitable carboxylic acid in the presence of an appropriate coupling agent, acid anhydride or acid chloride in an inert solvent.

A compound of formula A in which either or both of $R_1$ and $R_2$ includes a —$CO_2$H group may be converted into a compound of formula A wherein the corresponding substituent is esterified, for example by treating the carboxylic acid with a suitable $C_1$–$C_6$ alkyl alcohol in the presence of 1,3-dicyclohexylcarbodiimide in an inert solvent.

A compound of formula A in which either or both of $R_1$ and $R_2$ includes a free —$CO_2$H group may be converted into a compound of formula A in which the corresponding substituent is a group —CON($R_{11}R_{12}$), wherein $R_{11}$ and $R_{12}$ are as defined above, for example by treatment with ammonia or an amine in the presence of 1,3-dicyclohexylcarbodiimide in an inert solvent.

A compound of formula A in which either or both of $R_1$ and $R_2$ includes a free —$CO_2$H group may be converted into a compound of formula A wherein the corresponding substituent is a —$CH_2$OH group by reduction, for example using borane in a suitable solvent such as tetrahydrofuran.

A compound of formula A in which either or both of $R_1$ and $R_2$ is a nitro group may be converted into a compound of formula A in which the corresponding substituent is an amino group by reduction under standard conditions, for example by catalytic hydrogenation.

Protecting groups for substituents on $R_1$ and/or $R_2$ in any of the compounds of formulae (I), (I'), (II) and (III) are optionally introduced prior to step (i) or step (ii) when either or both $R_1$ and $R_2$ include one or more groups which are sensitive to the condensation reaction conditions or incompatible with the condensation reaction, for example a —COOH, —$CH_2$OH or amino group. The protecting groups are then removed at the end of the process. Any conventional protecting group suitable for the group $R_1$ and/or $R_2$ in question may be employed, and may be introduced and subsequently removed by well-known standard methods.

The condensation reaction between compounds (I) and (II) or (I') and (III) is suitably performed in the presence of a base which is potassium t-butoxide, sodium hydride, potassium carbonate, sodium carbonate, caesium carbonate, sodium acetate, potassium fluoride on alumina, or triethylamine in a solvent such as dimethylformamide, potassium t-butoxide in t-butanol, or a mixture of t-butanol and dimethylformamide (DMF). The reaction is typically performed at a temperature from 0° C. to the reflex temperature of the solvent.

The compounds of formula (I) may be prepared by a process comprising reacting 1,4-diacetyl-2,5-piperazinedione with a compound of formula (III) as defined above, in the presence of a base in an organic solvent. Similarly, the compounds of formula (I') may be prepared by a process which comprises reacting 1,4-diacetyl-2,5-piperazinedione with a compound of formula (II) as defined above, in the presence of a base in an organic solvent.

If necessary, the resulting compound of formula (I) or (I') can be separated from other reaction products by chromatography.

The reaction of 1,4-diacetyl-2,5-piperazinedione with the compound of formula (III) or (II) is suitably performed under the same conditions as described above for the condensation between compounds (I) and (II), or (I') and (III).

The substituted aldehydes of formulae (II) and (III) are known compounds or can be prepared from readily available starting materials by conventional methods. The 1,4-diacetyl-2,5-piperazinedione used as a starting material in the preparation of compounds of formula (I) may be prepared by treating 2,5-piperazinedione (glycine anhydride) with an acetylating agent. The acetylation may be performed using any conventional acetylating agent, for example acetic anhydride under reflux or, alternatively, acetic anhydride at a temperature below reflux in the presence of 4-dimethylaminopyridine.

Compounds of formula (I) may also be prepared by the microwave irradiation of a mixture comprising 1,4-diacetyl-2,5-piperazinedione, a compound of formula (III) and potassium fluoride on alumina (as base) in the absence of solvent.

Compounds of formula (I) may alternatively be prepared directly from 2,5-piperazinedione (glycine anhydride) by a process which comprises treating the 2,5-piperazinedione with a mixture comprising a compound of formula (III), sodium acetate and acetic anhydride at an elevated temperature, for example under reflux.

Compounds of formula (I') may be prepared by analogous processes, replacing compound (III) in each case by a compound of formula (II).

Compounds of formula A may also be prepared by a process comprising the microwave irradiation of (i) a mixture comprising a compound of formula (I) as defined above, a compound of formula (II) and potassium fluoride on alumina, or (ii) a mixture comprising a compound of formula (I') a compound of formula (III) and potassium fluoride on alumina, or (iii) a mixture comprising 1,4-diacetyl-2,5-piperazinedione, a compound of formula (II), a compound of formula (III) and potassium fluoride on alumina. The irradiation is performed in the absence of a solvent.

Compounds of formula (A) may also be obtained directly by a process which comprises condensing together 1,4- diacetyl-2,5-piperazinedione, a compound of formula (II) and a compound of formula (III) in the presence of a base in an organic solvent. Suitable bases, solvents and reaction conditions are as described above for the condensation reaction between, for example, compounds (I) and (II).

An alternative direct process for the preparation of compounds of formula (A) comprises condensing together 2,5-piperazinedione, a compound of formula (II) and a compound of formula (III) in the presence of sodium acetate and acetic anhydride at elevated temperature, for example under reflux.

An alternative process for the preparation of compounds of formula (I) comprises treating a compound of formula (V):

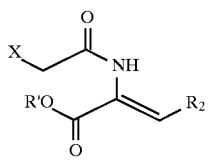

wherein $R_6$ to $R_{10}$ are as defined above, X is a halogen and R' is a $C_1$–$C_6$ alkyl group, with ammonia followed by acetic anhydride.

Compounds of formula (I') may be prepared by an analogous process which comprises treating a compound of formula (V'):

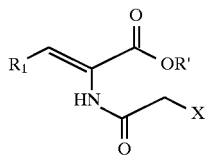

wherein $R_1$ to $R_5$, X and R' are as defined above, with ammonia followed by acetic anhydride.

X in formula (V) or (V') is typically iodine. R' is, for example, a $C_1$–$C_4$ alkyl group such as a methyl, ethyl, propyl, i-propyl, butyl, sec-butyl or tert-butyl group.

A review of synthetic approaches to unsaturated 3-monosubstituted and 3,6-disubstituted-2,5-piperazinediones is provided in Heterocycles, 1983, 20, 1407 (C.Shin).

Compounds of formula (A) may be optionally washed after any of the above preparative procedures with one or more of the following: water, ethanol, ethyl acetate and diethyl ether.

Where appropriate compounds of formula (A) may be optionally recrystallised from a suitable solvent such as methanol or acetic acid.

Compounds of formula (A) may be converted into pharmaceutically acceptable salts, and salts may be converted into the free compound, by conventional methods Suitable salts include salts with pharmaceutically acceptable, inorganic or organic, acids or bases. Examples of inorganic bases include ammonia and carbonates, hydroxides and hydrogen carbonates of group I and group II metals such as sodium, potassium, magnesium and calcium. Examples of organic bases include aliphatic and aromatic amines such as methylamine, triethylamine, benzylamine, dibenzylamine or α- or β-phenylethylamine, and heterocyclic bases such as piperidine, 1-methylpiperidine and morpholine. Examples of inorganic acids include hydrochloric acid, sulphuric acid and orthophosphoric acid. Examples of organic acids include p-toluenesulphonic acid, methansulphonic acid, mucic acid and succinic acid.

Compounds of formula (A) may also be converted into pharmaceutically acceptable esters. Suitable esters include branched or unbranched, saturated or unsaturated $C_1$–$C_6$ alkyl esters, for example methyl, ethyl and vinyl esters.

The diketopiperazines of formula (A), both novel and known and their pharmaceutically acceptable salts and esters (referred to hereinafter as the "present compounds") have utility as inhibitors of PAI. Elevated levels of PAI-1, by reducing the net endogenous fibrinolytic capacity, can contribute to the pathogenesis of various thrombotic disorders including myocardial infarction, deep vein thrombosis and disseminated intravascular coagulation. The present compounds therefore can act as inhibitors of the tPA/PAI-1 interaction. The present compounds can be used in the treatment of haemostatic disorders. A human or animal, e.g. a mammal, can therefore be treated by a method comprising administration of a therapeutically effective amount of a diketopiperazine of formula (A) or a pharmaceutically or veterinarily acceptable salt thereof.

Tissue plasminogen activator (tPA) is used as a fibrinolytic agent in the treatment of thrombotic disorders. The efficacy of the tPA in this role may be enhanced if it is administered together with a PAI inhibitor. A human or animal, e.g. a mammal, can therefore be treated by a method comprising the combined administration of a therapeutically effective amount of tPA and a therapeutically effective amount of any one of the present compounds. The present invention also provides products containing a diketopiperazine of formula (A) or a pharmaceutically acceptable salt or ester thereof and tPA as a combined preparation for simultaneous, separate or sequential use in the treatment of thrombotic disorders, for example where there is inappropriate PAI activity. In such products the present compound is formulated for oral or parenteral (intravenous, intramuscular or subcutaneous) administration and the tPA is formulated for intravenous administration.

As one example, during acute myocardial infarction (MI) one of the present compounds may be administered to a patient together with tPA to enhance the efficacy of the tPA treatment. As a further example, early re-occlusion following treatment of a patient with tPA may be prevented by the post-MI administration of one of the present compounds.

The compounds of formula (A) have been tested in a PAI functional assay. In this assay, a compound is incubated with PAI-1 prior to addition to the tPA assay system. Inhibition of PAI-1 results in the production of plasmin from plasminogen. In turn, plasmin cleaves the chromogenic substrate S2251 (Kabi Vitrum) producing pNA (p-nitroaniline) which is detected spectrophotometrically at 405 nm (K. Nilsson et al, Fibrinolysis (1987) 1, 163–168). The results of the assay are reported below.

The present compounds can be administered in a variety of dosage forms, for example orally such as in the form of tablets, capsules, sugar- or film-coated tablets, liquid solutions or suspensions or parenterally, for example intramuscularly, intravenously or subcutaneously. The present compounds may therefore be given by injection or infusion.

The dosage depends on a variety of factors including the age, weight and condition of the patient and the route of administration. Typically, however, the dosage adopted for each route of administration when a compound of the invention is administered alone to adult humans is 0.001 to 10 mg/kg, most commonly in the range of 0.01 to 5 mg/kg, body weight. Such a dosage may be given, for example, from 1 to 5 times daily by bolus infusion, infusion over several hours and/or repeated administration.

When one of the present compounds is administered in combination with tPA to adult humans, the dosage adopted for each route of administration is typically from 0.001 to 10 mg, more typically 0.01 to 5 mg per kg body weight for a compound of the invention and from 5 to 500 mg administered intravenously for the tPA. A suitable dosage regimen for the tPA is 100 mg given intravenously over 3 hours as follows: 10% of the total dose as an i.v. bolus over 1–2 minutes, 50% of the total dose as an infusion over 1 hour, 40% of the total dose as an infusion over the subsequent 2 hours.

A diketopiperazine of formula (A) or a pharmaceutically acceptable salt or ester thereof is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. An agent for use as an inhibitor of PAI comprising any one of the present compounds is therefore provided.

For example, the solid oral forms may contain, together with the active compound, diluents such as lactose, dextrose, saccharose, cellulose, corn starch or potato starch; lubricants such as silica, talc, stearic acid, magnesium or calcium stearate and/or polyethylene glycols; binding agents such as starches, arabic gums, gelatin, methylcellulose, carboxymethylcellulose, or polyvinyl pyrrolidone; disintegrating agents such as starch, alginic acid, alginates or sodium starch glycolate; effervescing mixtures; dyestuffs; sweeteners; wetting agents such as lecithin, polysorbates, lauryl sulphates. Such preparations may be manufactured in known manners, for example by means of mixing, granulating, tabletting, sugar coating, or film-coating processes.

Liquid dispersions for oral administration may be syrups, emulsions and suspensions. The syrups may contain as carrier, for example, saccharose or saccharose with glycerol and/or mannitol and/or sorbitol. In particular, a syrup for diabetic patients can contain as carriers only products, for example sorbitol, which do not metabolise to glucose or which only metabolise a very small amount to glucose. The suspensions and the emulsions may contain as carrier, for example, a natural gum, agar, sodium alginate, pectin, methylcellulose, carboxymethylcellulose or polyvinyl alcohol.

Suspensions or solutions for intramuscular injections may contain, together with the active compound, a pharmaceutically acceptable carrier such as sterile water, olive oil, ethyl oleate, glycols such as propylene glycol, and, if desired, a suitable amount of lidocaine hydrochloride. Some of the present compounds are insoluble in water. A compound may be encapsulated within liposomes.

TESTING OF THE PRESENT COMPOUNDS AS PAI INHIBITORS

Compounds of formula (A) were tested in a PAI chromogenic substrate assay. In the assay (K. Nilsson, Fibrinolysis (1987) 1, 163–168) each compound was incubated with PAI-1 prior to addition to the tPA assay system. Inhibition of PAI-1 by the compound of formula (A) resulted in the production of plasmin from plasminogen. In turn, the plasmin cleaved the chromogenic substrate S2251 (Kabi-Vitrum) producing pNA (p-nitroaniline) which was detected scectrophotometrically at 405 nm.

The degrees of inhibition observed in the chromogenic substrate assay at various concentrations, and/or $IC_{50}$ values, of compounds of formula (A) are presented in Table 1. $IC_{50}$ values for some compounds, not shown in Table 1, are listed in Table 2 which follows Table 1.

TABLE 1

INHIBITION OF PAI-1 IN THE S2251 CHROMOGENIC SUBSTRATE ASSAY

| Compound No. | Concentration in $\mu$m | | | | |
|---|---|---|---|---|---|
| | 100 | 50 | 25 | 12.5 | 6.25 |
| 1470 | 70 | 20 | 2 | 0 | 0 |
| 1471 | 80 | 60 | 20 | 6 | 0 |
| 1474 | 64 | 52 | 28 | | |
| 1476 | 68 | 48 | 18 | | |
| 1506 | 75 | 58 | 26 | 4 | 2 |
| 1507 | 78 | 62 | 45 | 1 | 1 |
| 1509 | 58 | 35 | 1 | 1 | 1 |
| 1542 | 75 | 41 | 9 | 1 | 1 |
| 1545 | 87 | 64 | 39 | 5 | 1 |
| 1560 | 50 | 48 | 46 | 34 | 13 |
| 1618 | 51 | 32 | 3 | 1 | |
| 1649 | 34 | 0 | 1 | 0 | |
| 1657 | 53 | 60 | 46 | 2 | |
| 1672 | 70 | 44 | 13 | 4 | 1 |
| 1676 | 29 | 51 | 52 | 12 | 1 |
| 1693 | 89 | 2 | 1 | 0 | |
| 1718 | 62 | 1 | 0 | 0 | 1 |
| 1808 | 76 | 48 | 73 | 2 | 1 |
| 1809 | 81 | 76 | 84 | 7 | 1 |
| 1845 | 14 | 30 | 49 | 60 | 53 |
| 1884 | 40 | 14 | 0 | 0 | 0 |
| 1886 | 42 | 40 | 18 | 6 | 0 |
| 1891 | 28 | 36 | 17 | 3 | 3 |
| 1910 | 27 | 36 | 50 | 61 | 63 |
| 1912 | 30 | 55 | 29 | 22 | 17 |
| 1921 | 65 | 43 | 25 | 14 | 16 |
| 1922 | 13 | 11 | 26 | 13 | 14 |
| 1923 | 38 | 31 | 20 | 12 | 13 |
| 1926 | 36 | 35 | 12 | 6 | 10 |
| 1927 | 33 | 39 | 20 | 22 | 14 |
| 1928 | 67 | 60 | 47 | 24 | 19 |
| 1929 | 27 | 45 | 59 | 48 | 16 |
| 1930 | 54 | 61 | 79 | 38 | 30 |
| 1959 | 5 | 1 | 2 | 2 | 1 |
| 1975 | 7 | 0 | 0 | 0 | 0 |
| 1976 | 3 | 0 | 0 | 0 | 0 |
| 1950 | 19 | 3 | 2 | 2 | 1 |
| 1982 | 48 | 49 | 28 | 6 | 1 |
| 1983 | 34 | 14 | 0 | 0 | 0 |

| Compound No. | Concentration in $\mu$M | | | $IC_{50}$ |
|---|---|---|---|---|
| | 100 $\mu$M | 50 $\mu$M | 20 $\mu$M | |
| 5023 | | | 1 | |
| 5026 | 34 | | 10 | |
| 5027 | 12 | 8 | 8 | |
| 5028 | 11 | 4 | 4 | |
| 5030 | 20 | 7 | 6 | |
| 5032 | 65 | 62 | 63 | 25.0–12.0 |
| 5040 | 0 | 1 | 0 | |
| 5041 | 1 | 0 | 0 | |
| 5042 | 77 | 64 | 42 | 20.0–10.0 |
| 5043 | 21 | 15 | 1 | |
| 5048 | 55 | 19 | 11 | 100.0–50.0 |
| 5052 | 77 | 76 | 86 | 12.0–6.0 |
| 5053 | 68 | 64 | 56 | 25.0–12.0 |
| 5054 | 5 | 57 | 48 | 50.0–25.0 |
| 5055 | 69 | 69 | 70 | 6.0–3.0 |
| 5057 | 44 | 29 | 37 | |
| 5061 | 43 | 48 | 60 | 25.0–12.0 |
| 5062 | 78 | 81 | 87 | 12.0–6.0 |
| 5069 | 70 | 71 | 75 | 10.0–5.0 |
| 5071 | 80 | 82 | 73 | 10.0–5.0 |
| 5072 | 60 | 61 | 61 | 10.0–5.0 |
| 5073 | 63 | 70 | 14 | 20.0–10.0 |
| 5074 | 47 | 57 | 26 | 20.0–10.0 |
| 5075 | 88 | 88 | 52 | 25.0–12.0 |
| 5077 | 34 | 46 | 42 | |
| 5078 | 60 | 67 | 11 | 20.0–10.0 |
| 5079 | 44 | 58 | 14 | 20.0–10.0 |
| 5081 | 25 | 34 | 50 | 6.0–3.0 |

TABLE 1-continued

INHIBITION OF PAI-1 IN THE S2251 CHROMOGENIC SUBSTRATE ASSAY

| | | | |
|---|---|---|---|
| 5188 | 90 | 94 | 3.50 |
| 5200 | 10 | 10 | |
| 5205 | 56 | 33 | 100.0 |
| 5206 | 72 | 78 | 3.0 |
| 5299 | | | 7.00 |
| 5324 | | | 9.00 |
| 5327 | | 17 | |
| 5335 | | | 22.0 |
| 5367 | | | 18.00 |
| 5371 | | | 12.00 |
| 5376 | | | 12.00 |
| 5379 | | 65 | 15.00 |
| 5386 | | | 18.00 |
| 5388 | | 58 | 9.00 |
| 5388.HCl | | 60 | 12.00 |
| 5389 | | 55 | 2.50 |
| 5389.HCl | | 57 | 2.50 |
| 5391 | | 64 | 6.50 |
| 5391.HCl | | 100 | 3.50 |
| 5393 | | 76 | 14.00 |
| 5393.HCl | | 58 | 20.00 |
| 5394 | | 59 | 16.00 |
| 5394.HCl | | 62 | 17.00 |
| 5397 | | 42 | |
| 5397.HCl | | 21 | |
| 5402 | | 37 | |
| 5402.HCl | | 37 | |

TABLE 2

| Compound No. | IC50 ($\mu$m) |
|---|---|
| 1470 | 50.0–100.0 |
| 1471 | 25.0–50.0 |
| 1474 | 25.0–50.0 |
| 1476 | 50.0–100.0 |
| 1506 | 25.0–50.0 |
| 1507 | 25.0–50.0 |
| 1509 | 50.0–100.0 |
| 1542 | 50.0–100.0 |
| 1560 | 50.0–100.0 |
| 1618 | 50.0–100.0 |
| 1652 | 25.0–50.0 |
| 1657 | 25.0–50.0 |
| 1672 | 50.0–100.0 |
| 1676 | 12.0–25.0 |
| 1693 | 50.0–100.0 |
| 1718 | 50.0–100.0 |
| 1808 | 25.0–12.0 |
| 1809 | 25.0–12.0 |
| 1845 | 10.0–5.0 |
| 1888 | 50.0–100.0 |
| 1910 | 5.0–10.0 |
| 1912 | 25.0–50.0 |
| 1921 | 100.0–50.0 |
| 1928 | 25.0–50.0 |
| 1929 | 25.0–12.0 |
| 1930 | 25.0–12.0 |
| 1982 | 50.0–25.0 |

REFERENCE EXAMPLE 1

Preparation of (3Z)-1-acetyl-3-benzylidene-2,5-piperazinedione 1,4-Diacetyl-2,5-piperazinedione (25.0 g, 126 mmol), which is compound (8) mentioned in Reference Example 3, was heated at 120°–130° C. in DMF (200 ml) with triethylamine (17.6 ml, 126 mmol) and benzaldehyde (13.0 ml, 126 mmol). After 4 h the mixture was cooled to room temperature and poured into EtOAc (1000 ml), and washed three times with brine. Any solid formed at this stage was filtered off.

The filtrate was dried (MgSO$_4$) and the solvent removed in vacuo. The residue was recrystallised from EtOAc:Hexane to give 11.78 g (38%) of the title compound as a yellow solid.

$^1$H NMR (CDCl$_3$ 400 MHz) δ=2.69 (3H, s) 4.54 (2H, s) 7.20 (1H, s) 7.40 (3H, m), 7.48 (2H, m), 7.93 (1H, br.s)

MS(DCI,NH$_3$): 262 (MNH$_4^+$, 20%), 245 (MH$^+$, 53%), 220 (52%), 204 (1006), 203 (100%)

| Microanalysis | C | H | N |
|---|---|---|---|
| Calc | 63.93 | 4.95 | 11.47 |
| Found | 64.11 | 5.02 | 11.41 |
| Found | 64.05 | 4.90 | 11.44 |

Alternatively (3Z)-1-acetyl-3-benzylidene-2,5-piperazinedione can be produced as follows:

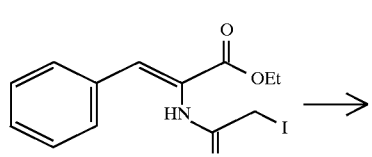

(16)

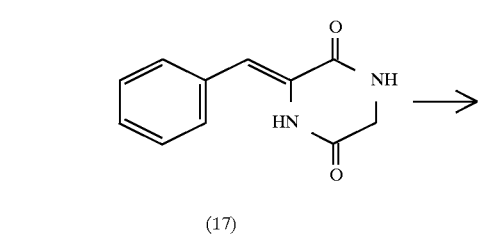

(17)

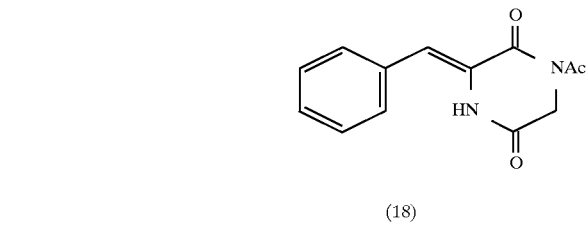

(18)

Compound 16 is treated with ammonia and subsequently with acetic anhydride to yield the title compound.

REFERENCE EXAMPLE 2

Preparation of (3Z)-1-acetyl-3-(4-acetamidobenzylidene)-2,5-piperazinedione 1,4-Diacetyl-2,5-piperazinedione (10.0 g, 50 mmol), prepared by the published procedure mentioned in Example 3, was stirred in DMF (40 ml) with 4-acetamidobenzaldehyde (8.24 g, 50 mmol) and triethylamine (7 ml, 50 mmol) and heated to 120° C. After 2½ h the mixture was cooled to room temperature, diluted with EtOAc (100 ml) and stirred overnight. The solid formed was collected, washed with EtOAc and dried to give 8.46 g (56%) of a yellow solid.

$^1$H NMR (CDCl$_3$+TFA, 400 MHz) δ=2.32 (3H, s) 2.72 (3H, s) 4.68 (2H, s) 7.36 (1H, s) 7.45 (2H, d, J=8 Hz) 7.60 (2H, d, J=8 Hz)

| Microanalysis | C | H | N |
|---|---|---|---|
| Calc | 59.80 | 5.02 | 13.95 |
| Found | 60.08 | 5.09 | 13.89 |
|  | 60.11 | 5.07 | 13.86 |

REFERENCE EXAMPLE 3

Preparation of 1,4-Diacetyl-2,5-piperazinedione 1,4-Diacetyl-2,5-piperazine dione (8) was prepared by the published procedure (S. M. Marcuccio and J. A. Elix, *Aust. J. Chem.*, 1984, 37, 1791).

REFERENCE EXAMPLE 4

(3Z)-1-Acetyl-3-(4-methoxybenzylidene)-2,5-piperazinedione (3Z)-1-Acetyl-3-(4-methoxybenzylidene)-2,5-piperazinedione (9) was prepared by the published procedure (T. Yokoi, L.-M. Yang, T. Yokoi, R.-Y. Wu, and K.-H. Lee, *J. Antibiot.*, 1988, 41, 494).

REFERENCE EXAMPLE 5

Preparation of (3Z)-1-acetyl-3-(2,6-dichlorobenzylidene)-2,5-piperazinedione 1,4-Diacetyl-2,5-piperazinedione prepared by the published procedure mentioned in Reference Example 3, was stirred in DMF with 2,6-dichlorobenzaldehyde and triethylamine and heated to 120°–130° C. for 1–3 h. The title compound was obtained with a yield of 40%.

REFERENCE EXAMPLE 6

Preparation of (3Z)-1-acetyl-3-(4-(3-dimethylamino)propoxybenzylidene)-2,5-piperazinedione 1,4-Diacetyl-2,5-piperazinedione, prepared by the published procedure mentioned in Reference Example 3, was stirred in DMF with 4-(3-dimethylamino)propoxybenzaldehyde and triethylamine and heated to 120°–130° C. for 2–4 h to give the title compound.

By the same method, using 4-(2-dimethylamino)ethoxybenzaldehyde in place of the abovementioned aldehyde, (3Z)-1-acetyl-3-(4-(2-dimethylamino)ethoxybenzylidene)-2,5-piperazinedione was prepared.

REFERENCE EXAMPLE 7

(3Z,6Z)-3-(4-Hydroxybenzylidene)-6-(4-methoxybenzylidene)-2,5-piperazinedione (3Z,6Z)-3-(4-Acetoxybenzylidene)-6-(4-methoxybenzylidene)-2,5-piperazinedione was treated with aqueous sodium hydroxide in THF at room temperature for 8 hrs to give the title compound (1519) in 30% yield.

EXAMPLE 1

Preparation of 1470

3(Z)-1-Acetyl-3-benzylidene-2,5-piperazinedione (one equivalent), which is compound 18 prepared according to Reference Example 1, was treated with 1-tert-butoxycarbonylpyrrole-2-carboxaldehyde in the presence of $Cs_2CO_3$ (1–1.1 equivalents) in DMF at 80°–100° C. for 1–6 hours. The title compound was obtained in 24% yield.

The crude product was optionally, washed with water, methanol, ethyl acetate or diethylether and optionally recrystallised from methanol as appropriate.

By the same method, but replacing 1-tert-butoxycarbonylpyrrole-2-carboxaldehyde by the appropriately substituted aldehyde or benzaldehyde, the following compounds were prepared:

| Compound | Yield (%) |
|---|---|
| 1471 | 52 |
| 1652 | 37 |
| 1983 | 45 |
| 1921 | 54 |
| 1922 | 43 |
| 1924 | 44 |
| 1910 | 31 |
| 1926 | 27 |
| 1927 | 26 |
| 1928 | 20 |
| 1929 | — |
| 1930 | — |
| 1912 | 33 |
| 5032 | 50 |
| 5040 | 45 |
| 5043 | 24 |
| 5053 | 44 |
| 5054 | 22 |
| 5057 | 43 |
| 5058 | 16 |

EXAMPLE 2

Preparation of 1474

3(Z)-1-Acetyl-3-(4-methoxybenzylidene)-2,5-piperazinedione prepared according to Reference Example 4, was treated with 2-thiophenecarboxaldehyde in the presence of $Cs_2CO_3$ (1–1.1 equivalents) in DMF at 80°–100° C. for 1–6 hours. The title compound was obtained in 76% yield.

By the same method, but replacing 2-thiophenecarboxaldehyde by the appropriately substituted aldehyde, the following compounds were prepared:

| Compound | Yield (%) |
|---|---|
| 1476 | 54 |
| 1479 | 84 |
| 1506 | 67 |
| 1507 | 7 |

The crude product was optionally washed with water, methanol, ethyl acetate and diethylether and optionally recrystallised from acetic acid or methanol as appropriate.

EXAMPLE 3
Preparation of 1884

3(Z)-1-Acetyl-3-benzylidene-2,5-piperazinedione (1 equivalent), prepared according to Reference Example 1, was treated with cyclohexanecarboxaldehyde (4 equivalents) in the presence of 0.5M potassium tert-butoxide in tertiary butanol (2 equivalents) in DMF at 0°–100° C. for 2 hours. The title compound was obtained with a yield of 58%. Purification was effected by recrystallisation from acetic acid.

1672 was prepared as above but replacing the 3(Z)-1-acetyl- 3-benzylidene-2,5-piperazinedione with 3(Z)-1-acetyl-3-(4-acetamidobenzylidene)-2,5-piperazinedione. The reaction was maintained for 18 hours. A low yield was obtained.

EXAMPLE 4
Preparation of 1676

1-Acetyl-3-(4-acetamidobenzylidene)-2,5-piperazinedione (one equivalent), prepared according to Reference Example 2, was treated with cinnamaldehyde in the presence of $Cs_2CO_3$ (1–1.1 equivalents) in DMF at 80°–100° C. for 1–6 hours. The title compound was obtained in 46% yield.

EXAMPLE 5
Preparation of 1618

1,4-Diacetyl-2,5-piperazinedione, prepared by the published procedure mentioned in Reference Example 3, was stirred in DMF with 2-thiophenecarboxaldehyde (1 equivalent) and triethylamine (1 equivalent) at 120° C. for 2–4 h. (3Z)-1-Acetyl-3-(2-thenylidene)-2,5-piperazinedione was obtained with a yield of 36%.

(3Z)-1-Acetyl-3-(2-thenylidene)-2,5-piperazinedione (1 equivalent) was stirred in DMF with 3-1-tert-butoxycarbonylindole-3-carboxyaldehye (1 equivalent) in the presence of $Cs_2CO_3$ (1–1.1 equivalents) at 80°–100° C. for 2–3 h. The title compound was obtained with a yield of 14%.

EXAMPLE 6
Preparation of 1542

3(Z)-1-Acetyl-3-(2,6-dichlorobenzylidene)-2,5-piperazinedione (1 equivalent), prepared according to Reference Example 5 was treated with 3-furaldehyde (1 equivalent) in the presence of $Cs_2CO_3$ (1–1.1 equivalents) in DMF at 80°–100° C. for 2–5 hours. The title compound was obtained in 46% yield.

By the same method, but replacing 3-furaldehyde by the appropriately substituted aldehyde, 1560 was obtained with a yield of 39%.

EXAMPLE 7
Preparation of 1982

3(Z)-1-Acetyl-3-benzylidene-2,5-piperazinedione (1 equivalent), as prepared in Reference Example 1, was treated with 4-(N-(3-dimethylaminoethyl)-N-methyl) aminomethylbenzaldehyde in the presence of $Cs_2CO_3$ (1–1.1 equivalents) in DMF at 80°–100° C. for 1–6 h to give (3Z,6Z)-3-Benzylidene-6-(4-(N-(3-dimethylaminoethyl)-N-methyl)aminomethylbenzylidene)-2,5-piperazinedione in a yield of 50%.

Compound 1982, the hydrochloride salt of (3Z,6Z)-3-Benzylidene-6-(4-(N-(3-dimethylaminoethyl)-N-methyl) aminomethylbenzylidene)-2,5-piperazinedione, was prepared by bubbling HCl gas through a solution of the corresponding free base in THF, followed by evaporation to dryness. The yield was 45%.

EXAMPLE 8
Preparation of 1976

3(Z)-1-Acetyl-3-(4-(3-dimethylamino) propoxybenzylidene)-2,5-piperazinedione (1 equivalent), prepared according to Reference Example 6 was treated with 3-(imidazol-1-yl)benzaldehyde (1 equivalent) in the presence of $Cs_2CO_3$ (1–1.1 equivalent) in DMF at 80°–90° C. for 2–4 hours. The title compound was obtained in 52% yield.

EXAMPLE 9
Preparation of 1886

1519 (1 equivalent), prepared in Reference Example 7, was treated in DMF with sodium hydride (1 equivalent) and N-phthaloylglycyl chloride (1 equivalent) in DMF at room temperature for 4 h. The title compound was obtained with a yield of 30%.

EXAMPLE 10
Preparation of 5026

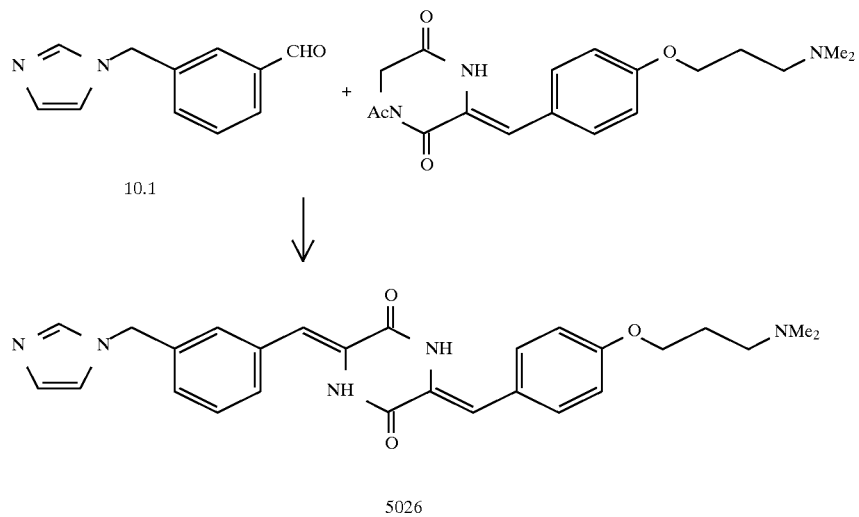

(3Z)-1-acetyl-3-(4-(3-dimethylamino) propoxybenzylidene)-2,5-piperazinedione, prepared as in Reference Example 6, was treated with compound 10.1 in dimethylformamide (DMF) in the presence of $Cs_2CO_3$ at a temperature of 80° C.–90° C. for 2–4 hours. Compound 5026 was obtained in 95% yield.

By an analogous process, using the appropriately substituted benzaldehyde in place of compound 10.1, the following compounds were prepared:

| Compound No. | Yield % |
|---|---|
| 5030 | 30 |
| 5048 | 72 |
| 5188 | 70 |

By the same method, but replacing 11.1 by the appropriately substituted aldehyde, the following compounds were prepared:

| Compound No. | Yield (%) |
|---|---|
| 5028 | 44 |
| 5029 | 25 |
| 5041 | 39 |
| 5042 | 39 |
| 5046 | 37 |
| 5052 | 58 |

EXAMPLE 12

Preparation of 5023

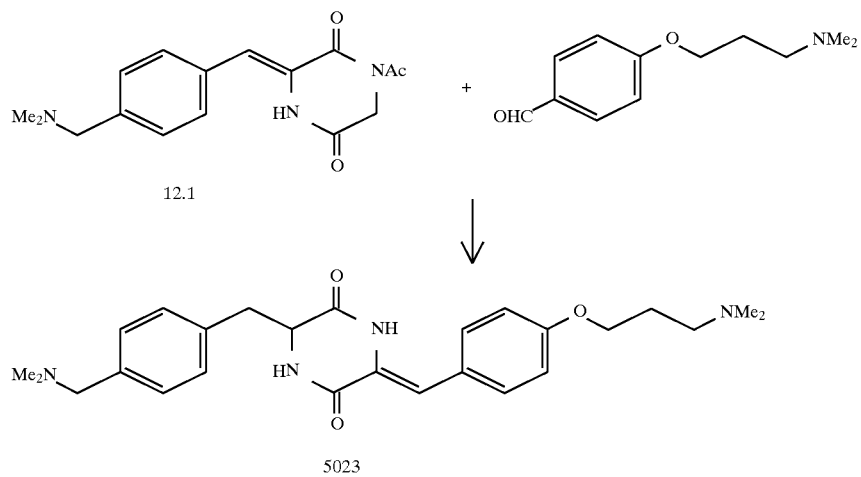

Compound 12.1 was treated with 4-(3-dimethylamino) propoxybenzaldehyde in DMF in the presence of $Cs_2CO_3$ at a temperature of 80° C.–90° C. for 2–4 hours. Compound 5023 was obtained in 36% yield.

EXAMPLE 11

Preparation of 5027

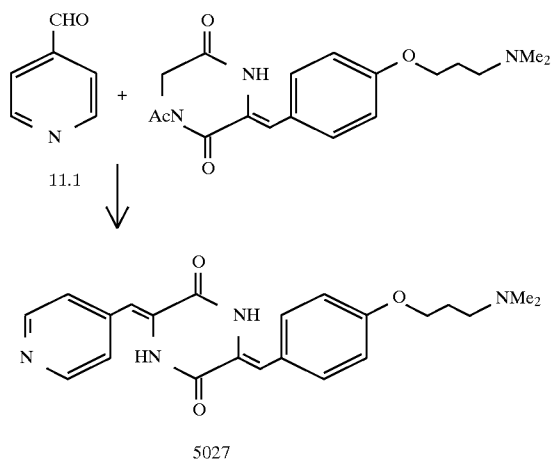

(3Z)-1-acetyl-3-(4-(3-dimethylamino) propoxybenzylidene)-2,5-piperazinedione, prepared as in Reference Example 6, was treated with compound 11.1 in DMF in the presence of $Cs_2CO_3$ at 80° C.–90° C. for 2–4 hours. Compound 5027 was produced in 33% yield.

EXAMPLE 13

Preparation of 5062

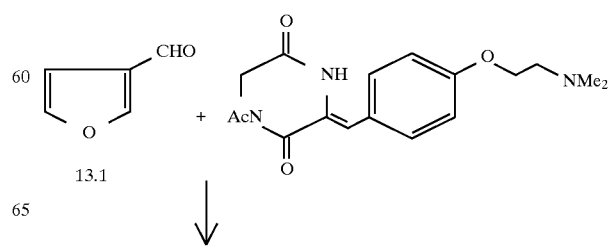

21
-continued

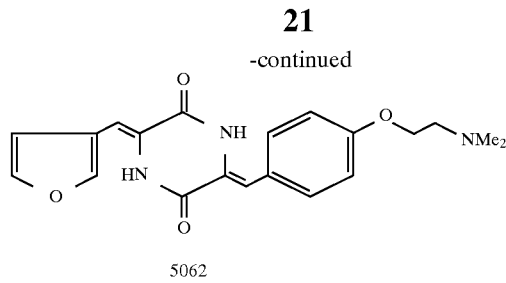

5062

(3Z)-1-acetyl-3-(4-(2-dimethylamino)ethoxybenzylidene)-2,5-piperazinedione, prepared as in Reference Example 6, was treated with compound 13.1 in DMF in the presence of $Cs_2CO_3$ at a temperature of 80° C.–90° C. for 2–4 hours. Compound 5062 was obtained in 12% yield.

By the same method, but using the appropriately substituted aldehyde in place of compound 13.1, the following compounds were prepared:

| Compound No. | Yield (%) |
|---|---|
| 5071 | 41 |
| 5072 | 86 |

EXAMPLE 14

Preparation of compounds of formula (I)

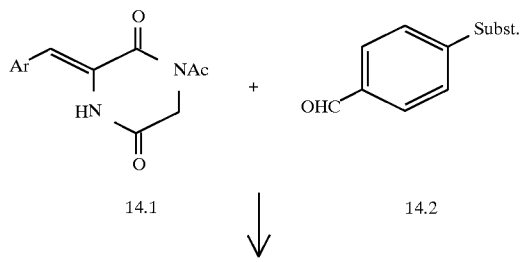

14.1  14.2

22
-continued

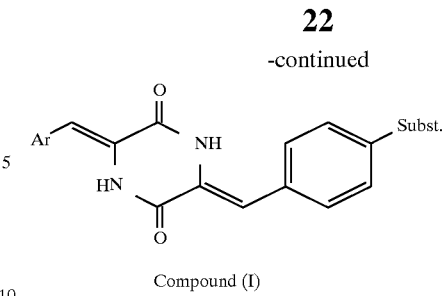

Compound (I)

The 2,5-piperazinedione derivative 14.1 was treated with the aldehyde 14.2, the groups Ar and Subst. being as specified below, in DMF in the presence of $Cs_2CO_3$ at 80° C.–90° C. for 2–4 hours. The compounds of formula (I) listed below were prepared:

| Ar | Subst. | Compound of formula (I) | Yield (%) |
|---|---|---|---|
| Phenyl | —$CH_2S(CH_2)_2NMe_2$ | 5058 | 16 |
| 3-furyl | —$CH_2S(CH_2)_2NMe_2$ | 5073 | 33 |
| 3-thienyl | —$CH_2S(CH_2)_2NMe_2$ | 5078 | 38 |
| 3-thienyl | —$CH_2NHC(O)CH_2NMe_2$ | 5074 | 83 |
| 2-bromophenyl | —$CH_2NHC(O)CH_2NMe_2$ | 5079 | 28 |
| 3-furyl | —$CH_2NHC(O)CH_2NMe_2$ | 5081 | 68 |
| 3-thienyl | —$CH_2O(CH_2)_2NMe_2$ | 5069 | 29 |
| 3-furyl | —$CH_2O(CH_2)_2NMe_2$ | 5077 | 20 |

EXAMPLE 15

Preparation of compounds of formula (I)

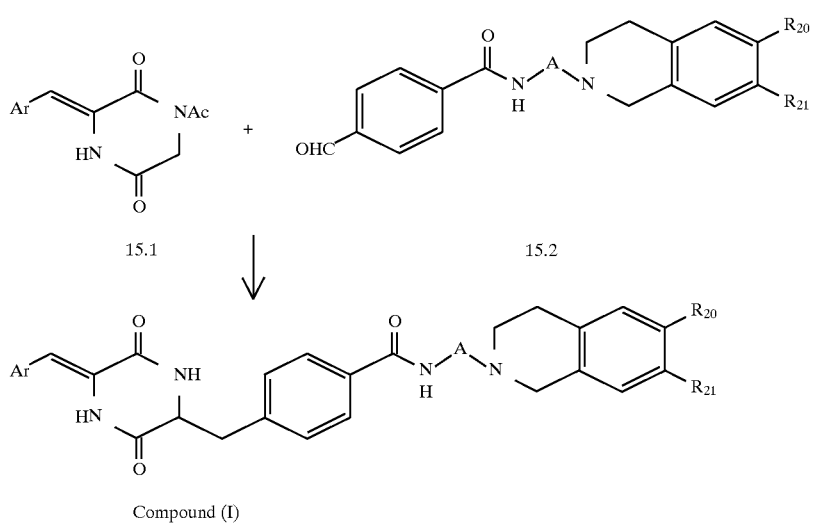

Compound (I)

The 2,5-piperazinedione derivative 15.1 was treated with the aldehyde 15.2 in which $R_{20}$ and $R_{21}$ are both H or are both OMe, the substituent Ar and linking group A being as specified below, in DMF in the presence of $Cs_2CO_3$ at 80° C. to 90° C. for 2–4 hours. The compounds of formula (I) listed below were prepared. In 5391, 5394 and 5371 $R_{20}$ and $R_{21}$ are both H. In 5393 and 5402 $R_{20}$ and $R_{21}$ are OMe.

| Ar | A | Compound of Formula (I) | Yield (%) |
|---|---|---|---|
| Phenyl | $-(CH_2)_2-$ | 5391 | 21 |
| Phenyl | $-(CH_2)_3-$ | 5394 | 47 |
| Phenyl | $-(CH_2)_4-$ | 5371 | 56 |
| Phenyl | 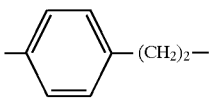 | 5393 | 44 |
| 4-nitrophenyl | 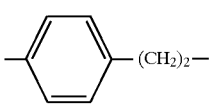 | 5402 | 62 |

EXAMPLE 16
Preparation of compounds of formula (I)

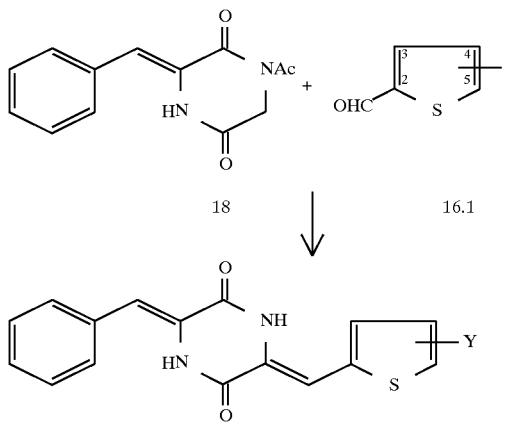

(3Z)-1-acetyl-3-benzylidene-2,5-dione prepared as in Reference Example 1 (compound 18), was treated with the aldehyde 16.1 in which substituent Y was as indicated below, in DMF in the presence of $Cs_2CO_3$ at 80° C.–90° C. for 2–4 hours. The compounds of formula (I) listed below were prepared:

| Y | Compound of formula (I) | Yield % |
|---|---|---|
| 5-O(CH$_2$)$_2$NMe$_2$ | 5324 | 34 |
| 4-O(CH$_2$)$_2$NMe$_2$ | 5327 | 51 |
| 5-(CH$_2$)$_2$NMe$_2$ | 5335 | 45 |
| 5-O(CH$_2$)$_2$O(CH$_2$)$_2$NMe$_2$ | 5388 | 12 |
| 5-O(CH$_2$)$_6$NMe$_2$ | 5389 | 35 |
| 5-N(Me)(CH$_2$)$_2$NMe$_2$ | 5299 | 2 |

By the same method, but using 2,5-dichlorothiophene-4-carboxaldehyde in place of compound 16.1, 5075 was prepared in 31% yield.

EXAMPLE 17
Preparation of salts

1. Hydrochloride salts of the following compounds of formula (I) were prepared by bubbling HCl gas through a solution of the corresponding free base in tetrahydrofuran (THF) at room temperature. The salt was recovered in the yield indicated.

| Compound of formula (I) | Hydrochloride salt | Yield (%) |
|---|---|---|
| 1975 | 5026 | 95 |
| 1976 | 5030 | 30 |
| 5048 | 5048.HCl | 72 |
| 5188 | 5206 | 24 |
| 5200 | 5205 | 31 |
| 5367 | 5376 | 47 |
| 5397 | 5397.2HCl | 36 |
| 5041 | 5041.HCl | 63 |
| 5042 | 5042.HCl | 51 |
| 5046 | 5046.HCl | 32 |
| 5052 | 5052.HCl | 58 |
| 5023 | 1988 | 50 |
| 5062 | 5062.HCl | — |
| 5071 | 5071.HCl | — |
| 5072 | 5072.HCl | — |
| 1910 | 5055 | 57 |
| 1912 | 5061 | 47 |
| 5032 | 5032.HCl | 39 |
| 5053 | 5053.HCl | 90 |
| 5054 | 5053.HCl | 88 |
| 5073 | 5073.HCl | 76 |
| 5078 | 5078.HCl | 78 |
| 1912 | 5061 | 47 |
| 5074 | 5074.HCl | 51 |
| 5079 | 5079.HCl | 73 |
| 5081 | 5081.HCl | 76 |
| 5069 | 5069.HCl | — |
| 5077 | 5077.HCl | — |
| 5324 | 5324.HCl | 68 |
| 5336 | 5336.HCl | 74 |
| 5335 | 5335.HCl | — |
| 5388 | 5388.HCl | 79 |
| 5389 | 5389.HCl | 75 |
| 5391 | 5391.HCl | — |
| 5394 | 5394.HCl | 75 |
| 5371 | 5379 | 65 |

2. Hydrochloride salts of the following compounds of formula (I) were prepared by bubbling HCl gas through a solution of the corresponding free base in hot DMF. The salt was recovered in the yield indicated.

| Compound of formula (I) | Hydrochloride salt | Yield |
|---|---|---|
| 5386 | 5386.2HCl | 79 |
| 5393 | 5393.HCl | 60 |
| 5402 | 5402.HCl | 52 |

3. Hydrochloride salts of the following compounds of formula (I) were prepared by treating the free base with 2M HCl:

| Compound of formula (I) | Hydrochloride salt | Yield (%) |
|---|---|---|
| 5027 | 5027.HCl | 67 |
| 5028 | 5028.HCl | 92 |
| 5029 | 5029.HCl | 76 |
| 5040 | 5040.HCl | 90 |

4. 5043.HCl, the hydrochloride salt of 5043, was prepared by bubbling HCl gas through a solution of 5043 in MeOH.

5057.HCl, the salt of 5057, was prepared by bubbling HCl gas through a solution of 5057 in THF following by recrystallisation from MeOH.

EXAMPLE 18
PHARMACEUTICAL COMPOSITION

Tablets, each weighing 0.15 g and containing 25 mg of a compound of the invention can be manufactured as follows:
Composition for 10,000 tablets compound of the invention (250 g)

lactose (800 g)

corn starch (415 g)

talc powder (30 g)

magnesium stearate (5 g)

The compound of the invention, lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium stearate is added, carefully mixed and processed into tablets.

EXAMPLE 19
Characterisation of compounds of formula A

The compounds prepared in the preceding Examples, were characterised by mass spectroscopic, microanalytical, proton nuclear magnetic resonance and, in some cases, infra-red techniques. The results are set out in the Tables which follow:

| No. | Mol. Formula | Mass spec. data mass (intensiy) | mode | $^1$H nmr data solvent (field) | δ |
|---|---|---|---|---|---|
| 1910 | $C_{23}H_{20}N_4O_3$ | 401(100) | CI | $d_6$-DMSO/400 MHz | 4.28–4.32(2H, t), 4.35–4.40(2H, t), 6.75–7.70(14H, m), 10.15(2H, brs). |
| 5023 | $C_{26}H_{32}N_4O_3$ | 449(100) | EI | $CDCl_3$/400 MHz | 2.00(2H, m), 2.25(12H, s), 2.46(2H, t), 3.45(2H, s), 4.05(2H, t), 6.95–7.42 (10H, m), 8.15(2H, brs). |
| 5026 | $C_{27}H_{29}N_5O_3 \cdot 2HCl$ | | | $d_6$-DMSO/400 MHz | 2.12(2H, m), 2.73(6H, s), .21(2H, m), 4.11(2H, t), 5.48(2H, s), 6.76(2H, s), 7.00(2H, d), 7.47(2H, d), 7.50(2H, d), 7.55(2H, d), 7.65(1H, s), 7.77(1H, s), 9.21(1H, s), 10.12(2H, brs), 10.45 (1H, brs). |
| 5027 | $C_{22}H_{24}N_4O_3 \cdot 2HCl$ | | | $CDCl_3 + CF_3CO_2H$/400 MHZ | 2.00(2H, t), 3.00(6H, s), 3.45(2H, m), 3.90(2H, t), 7.00(2H, d), 7.15(1H, s), 7.35(1H, s), 7.45(2H, d), 8.00(2H, d), 8.95(2H, d). |
| 5028 | $C_{22}H_{24}N_4O_3 \cdot 2HCl$ | | | $CDCl_3 + CF_3CO_2D$/400 MHz | 2.35(2H, m), 3.00(6H, s), 3.45(2H, t), 4.15(2H, t), 7.00(2H, d), 7.15(1H, s), 7.30(1H, s), 7.45(2H, d), 8.10(1H, t), 8.50(1H, d), 8.95(1H, d), 9.15(1H, s). |
| 5030 | | | | $d_6$-DMSO/400 MHz | 2.18(2H, m), 2.77(6H, s), 3.20(2H, m), 4.10(2H, t), 6.77(1H, s), 6.81(1H, s), 7.00(2H, d), 7.51(2H, d), 7.65(2H, m), 7.71(1H, m), 7.85(1H, s), 7.96(1H, s), 8.29(1H, s), 9.60(1H, s), 10.21 (1H, brs), 10.50(1H, brs), 10.61 (1H, brs). |
| 5032 | $C_{23}H_{25}N_3O_4 \cdot HCl$ | 408(20), 306(30) | CI | $d_6$-DMSO/400 MHz | 2.83(6H, s), 3.23(2H, m), 4.02(2H, d), 4.30(1H, m), 5.96(1H, brd), 6.77(1H, s), 6.78(1H, s), 7.02(2H, d), 7.33(1H, m), 7.42(2H, m), 7.55(4H, m), 9.70(1H, brs), 10.12(2H, br). |
| 5040 | $C_{25}H_{27}N_3O_5 \cdot HCl$ | 450(10) | CI | $d_6$-DMSO/400 MHz | 3.20–3.55(6H, m), 3.75–4.00(4H, m), 4.02 (2H, d), 4.39(1H, m), 5.99(1H, brs), 6.77 (1H, s), 6.78(1H, s), 7.02(2H, d), 7.33 (1H, m), 7.45(2H, m), 7.55(4H, m), 10.20 (3H, br) |
| 5041 | $C_{21}H_{23}N_3O_4 \cdot HCl$ | 382(100) | EI | $d_6$-DMSO/400 MHz | 2.09(2H, m), 2.80(6H, s), 3.20(2H, m), 4.09(2H, t), 6.63(1H, s), 6.64(1H, m), 6.78(1H, s), 6.89(1H, m), 7.0(2H, d), 7.54(2H, d), 7.90(1H, s), 9.45(1H, brs), 9.75(1H, brs), 10.14(1H, brs) |
| 5042 | $C_{21}H_{23}N_3O_3S \cdot HCl$ | 398(35) | EI | $d_6$-DMSO/400 MHz | 2.09(2H, m), 2.79(6H, s), 3.18(2H, m), 4.10(2H, t), 6.76(1H, s), 6.85(1H, s), 7.00(2H, d), 7.41(1H, m), 7.51(2H, d), 7.62(1H, m), 7.94(1H, m), 9.89(1H, brs), 9.92(1H, brs), 10.10(1H, brs). |
| 5043 | $C_{27}H_{32}N_4O_5 \cdot HCl$ | 493(100) | CI | $d_6$-DMSO/400 MHz | 3.01–3.85(14H, m), 4.02(2H, d), 4.40 (1H, brs), 6.77(1H, s), 6.78(1H, s), 7.02 (2H, d), 7.32(1H, m), 7.42(2H, m), 7.55 (4H, m), 10.20(2H, s). |
| 5046 | $C_{21}H_{23}N_3O_3S \cdot HCl$ | 398(23), 169(100) | EI | $d_6$-DMSO/400 MHz | 2.09(2H, m), 7.28(6H, s), 3.12(2H, m), 4.10(2H, t), 6.78(1H, s), 6.94(1H, s), 7.00(2H, d), 7.18(1H, m), 7.54(2H, d) |

-continued

| | | | | | |
|---|---|---|---|---|---|
| | | | | | 7.58(1H, m), 7.76(1H, m), 9.75(1H, brs), 10.16(1H, brs). |
| 5048 | $C_{25}H_{28}N_4O_4 \cdot HCl$ | 485(100) | EI | $d_6$-DMSO/400 MHz | 2.05(2H, s), 2.14(2H, m), 2.79(6H, d), 3.20(2H, m), 4.13(2H, t), 6.70(1H, s), 6.75(1H, s), 7.0(2H, d), 7.48(2H, d), 7.51(2H, d), 7.62(2H, d), 9.94(1H, brs), 10.15(1H, brs), 10.20(1H, brs). |
| 5052 | | | | $d_6$-DMSO/400 MHz | 2.15(2H, m), 2.28(6H, s), 3.20(2H, m), 4.10(2H, t), 6.68(1H, s), 6.75(1H, s), 6.94(1H, s), 7.00(2H, d), 7.54(2H, d), 7.76(1H, s), 8.23(1H, s). |
| 5053 | $C_{24}H_{25}N_3O_3 \cdot HCl$ | | | $CDCl_3 + CF_3CO_2D$/400 MHz | 2.20(4H, m), 3.20(2H, m), 3.70(2H, m), 4.00(2H, m), 4.45(2H, t), 7.00(2H, d), 7.23(1H, s), 7.39(1H, s), 7.45(7H, m). |
| 5054 | $C_{24}H_{25}N_3O_4 \cdot HCl$ | | | $CDCl_3 + CF_3CO_2D$/400 MHz | 3.25(2H, m), 3.67(2H, m), 3.85(2H, m), 4.05–4.20(4H, m), 4.47(2H, m), 6.97 (2H, d) 7.20(1H, s), 7.26(1H, s), 7.39–7.51(7H, m). |
| 5055 | $C_{23}H_{20}N_4O_3 \cdot HCl$ | 401(100) | ESI | $d_6$-DMSO/400 MHz | 4.40(2H, t), 4.60(2H, t), 6.73(1H, s), 6.75(1H, s), 6.99(2H, d), 7.30–7.55 (7H, m), 7.65(1H, s), 7.90(1H, s), 9.10 (1H, s), 10.10(1H, s), 10.15(1H, s), 10.20(1H, brs) |
| 5057 | $C_{24}H_{22}N_4O_4 \cdot HCl$ | | | $d_6$-DMSO/400 MHz | 4.00–4.05(2H, m), 4.20–4.32(2H, m), 4.48 (1H, m), 6.77(1H, s), 6.78(1H, s), 7.03 (2H, d), 7.32(2H, m), 7.42(2H, m), 7.55 (4H, m), 7.71(1H, m), 7.77(1H, m), 9.12 (1H, s), 10.20(2H, brs). |
| 5058.HCl | $C_{23}H_{25}N_3O_2S \cdot HCl$ | 409(15) | CI | $d_6$-DMSO/400 MHZ | 2.70–2.75(8H, m), 3.20–3.25(2H, m), 3.85 (2H, s), 6.78(2H, s), 7.32–7.55(9H, m), 9.68(1H, brs), 10.22(1H, s), 10.24 (1H, s) |
| 5061 | $C_{23}H_{24}N_4O_3 \cdot HCl$ | | | $d_6$-DMSO/400 MHz | 2.84(6H, s), 3.95(2H, s), 4.40(2H, d), 6.75(1H, s), 6.77(1H, s), 7.33–7.55 (9H, m), 9.15(1H, t), 9.85(1H, brs), 10.20(1H, brs), 10.25(1H, brs). |
| 5062 | $C_{20}H_{21}N_3O_4 \cdot HCl$ | | | $d_6$-DMSO/400 MHz | 2.76(6H, d), 3.51(2H, m), 4.38(2H, t), 6.66(1H, s), 6.75(1H, s), 6.91(1H, s), 7.05(2H, d), 7.55(2H, d), 7.74(1H, s), 8.22(1H, s), 9.76(1H, s). |
| 5069 | $C_{21}H_{23}N_3O_3S \cdot HCl$ | 397(10) | CI | $d_6$-DMSO/400 MHz | 2.80(6H, s), 3.30(2H, t), 3.76.(2H, t), 4.58(2H, t), 6.82(1H, s), 6.87(1H, s), 7.45(2H, m), 7.58(2H, d), 7.65(1H, m), 8.00(1H, s), 9.78(1H, s), 10.02(1H, s), 10.18(1H, s). |
| 5071 | $C_{20}H_{21}N_3O_3S \cdot HCl$ | | | $d_6$-DMSO/400 MHz | 2.86(6H, d), 3.53(2H, m), 4.38(2H, t), 6.78(1H, s), 6.84(1H, s), 7.07(2H, d), 7.43(1H, m), 7.58(2H, d), 7.65(1H, m), 7.96(1H, m), 9.55(1H, s), 10.05 (1H, brs), 10.13(1H, brs). |
| 5072 | $C_{21}H_{23}N_3O_3S_2 \cdot HCl$ | | | $d_6$-DMSO/400 MHz | 2.58(3H, s), 2.78(6H, s), 3.44(2H, m), 4.36(2H, t), 6.77(1H, s), 6.85(1H, s), 7.05(2H, d), 7.12(1H, d), 7.52(1H, d), 7.58(2H, d), 10.20(1H, s) |
| 5073 | $C_{21}H_{23}N_3O_3S$ | 398(15), 293(100) | EI | $CDCl_3 + CF_3CO_2D$/400 MHz | 2.75(2H, t), 2.90(6H, s), 3.25(2H, t), 3.78(2H, s), 6.70(1H, s), 7.10(1H, s), 7.40(4H, s), 7.60(1H, s), 7.85(1H, s). |
| 5073.HCl | $C_{21}H_{23}N_3O_3S \cdot HCl$ | | | $d_6$-DMSO/400 MHz | 2.75(6H, s), 2.75–2.80(2H, m), 3.20 (2H, m), 3.84(2H, s), 6.70(1H, s), 6.77 (1H, s), 6.90(1H, s), 7.40(2H, d), 7.52 (2H, d), 7.75(1H, s), 8.20(1H, s), 9.78 (1H, brs), 10.00(1H, s), 10.00(1H, brs) |
| 5074 | | | | $d_6$-DMSO/400 MHz | 2.82(6H, s), 4.00(2H, s), 4.41(2H, d), 6.81(1H, s), 6.88(1H, s), 7.98(2H, m), 9.15(1H, brs), 9.90(1H, brs), 10.04 (1H, brs), 10.18(1H, brs). |
| 5075 | $C_{16}H_{10}C_{12}N_2O_2S$ | | | $d_6$-DMSO/400 MHz | 6.50(1H, s), 6.80(1H, s), 7.35(1H, t), 7.39–7.45(3H, m), 7.55(2H, d). |
| 5077 | $C_{21}H_{23}N_3O_4 \cdot HCl$ | | | $d_6$-DMSO/400 MHz | 2.55(2H, t), 2.80(6H, s), 3.80(2H, t), 4.55(2H, s), 6.70(1H, s), 6.80(1H, s), 6.95(1H, s), 7.45(2H, d), 7.60(2H, d), 7.85(1H, s), 8.30(1H, s), 9.90(1H, s), 10.00(1H, s). |
| 5078 | $C_{21}H_{23}N_3O_2S_2$ | 414(15), 309(100) | EI | $CDCl_3 + CF_3CO_2D$/400 MHz | 2.75(2H, t), 2.88(6H, s), 3.25(2H, t), 3.88(2H, s), 7.22–7.28(3H, m), 7.45 (4H, s), 7.50–7.54(1H, m), 7.64)–7.66 (1H, s). |
| 5078. HCl | $C_{12}H_{23}N_3O_2S_2 \cdot HCl$ | | | $d_6$-DMSO/400 MHz | 2.72–2.78(2H, m), 2.75(6H, s), 3.20–3.25 (2H, m), 3.84(2H, s), 6.75(1H, s), 6.85 (1H, s), 7.40–7.45(3H, m), 7.55(2H, d), |

| | | | | | |
|---|---|---|---|---|---|
| | | | | | 7.64–7.67(1H, m), 7.96–7.99(1H, m), 9.85 (1H, brs), 10.05(1H, brs), 10.18 (1H, brs). |
| 5079 | $C_{23}H_{23}BrN_4O_3$.HCl | | | $d_6$-DMSO/400 MHz | 2.82(6H, s), 4.00(2H, s), 4.41(2H, d), 6.74(1H, s), 6.80(1H, s), 7.30(1H, m), 7.36(2H, d), 7.45(1H, m), 7.54(2H, d), 7.60(1H, d), 7.68(1H, d), 9.56(1H, brt), 9.90(1H, brs), 10.36(1H, brs), 10.48 (1H, brs). |
| 5081 | $C_{21}H_{22}N_4O_4$.HCl | | | $d_6$-DMSO/400 MHz | 2.83(6H, s), 4.01(2H, s), 4.39(2H, d), 6.68(1H, s), 6.79(1H, s), 6.94(1H, s), 7.35(2H, d), 7.54(2H, d), 7.76(1H, s), 8.22(1H, s), 9.12(1H, brt), 9.82 (2H, brs), 10.12(1H, brs). |
| 5188 | $C_{27}H_{27}N_3O_3$ | 442(100) | ESI | $d_6$-DMSO/400 MHz | 1.8–1.9(2H, m), 2.15(6H, s), 2.38 (2H, t), 4.05(2H, t), 6.78(1H, s), 6.90 (1H, s), 6.99(2H, d), 7.50–7.58(4H, m), 7.61–7.65(1H, m), 7.39–7.98(3H, m), 8.11 (1H, s), 10.28(2H, brs). |
| 5200 | $C_{27}H_{27}N_3O_3$ | 442(100) | ESI | $d_6$-DMSO/400 MHz | 1.81–1.91(2H, m), 2.15(6H, s), 2.35 (2H, t), 4.09(2H, t), 6.75(1H, s), 6.96 (2H, d), 7.21(1H, s), 7.5–7.65(7H, m), 7.94(2H, d), 10.15(2H, brs). |
| 5205 | $C_{27}H_{27}N_3O_3$.HCl | 442(40) | CI | $d_6$-DMSO/400 MHz | 2.12–2.20(2H, m), 2.80(6H, s), 3.20–3.25 (2H, m), 4.10(2H, t), 6.75(1H, s), 7.01 (2H, d), 7.24(1H, s), 7.51–7.67(6H, m), 7.92(2H, d), 7.98–8.01(1H, m), 10.1 (2H, brs), 10.25(1H, brs). |
| 5206 | $C_{27}H_{27}N_3O_3$.HCl | | | $d_6$-DMSO/400 MHz | 2.11–2.21(2H, m), 2.60(6H, s), 2.85–2.98 (2H, m), 4.09(2H, t), 6.78(1H, s), 6.94 (1H, s), 7.0(2H, d), 7.50–7.59(4H, m), 7.64(1H, d), 7.90–7.99(3H, m), 8.12 (1H, m), 10.21(1H, brs), 10.43(1H, brs). |
| 5324 | $C_{20}H_{21}N_3O_3S$.HCl | 384(100) | CI | $d_6$-DMSO/400 MHz | 2.85(6H, s), 3.52(2H, t), 4.50(2H, t), 6.52(1H, d), 6.78(1H, s), 6.81 (1H, s), 7.31(1H, d), 7.32(1H, m), 7.45(2H, m) 7.57(2H, d), 9.70(1H, s), 10.15(1H, s), 10.41(1H, brs). |
| 5327 | $C_{20}H_{21}N_3O_3S$ | 384(20) | CI | $d_6$-DMSO/400 MHz | 2.22(6H, s), 2.63(2H, t), 4.05(2H, t), 6.76(1H, s), 6.82(2x1H, s), 7.30(1H, s), 7.33(1H, m), 7.42(2H, m), 7.55(2H, d). |
| 5335 | $C_{20}H_{21}N_3O_2S$.HCl | 368(20) | CI | $d_6$-DMSO/400 MHz | 2.78(6H, s), 3.28(4H, m), 6.78(1H, s), 6.89(1H, s), 7.02(1H, d), 7.38–7.45 (4H, m), 7.55(2H, d), 9.68(1H, brs), 10.40(1H, br). |
| 5336 | $C_{20}H_{21}N_3O_3S$.HCl | 384(10) | CI | $d_6$-DMSO/400 MHz | 2.82(6H, s), 3.49(2H, t), 4.38(2H, t), 6.78(1H, s), 6.80(1H, s), 6.94(1H, s), 7.31(1H, s), 7.32(1H, m), 7.42(2H, m), 7.55(2H, d), 9.78(1H, s), 10.25(1H, s), 10.45(1H, brs). |
| 5367 | $C_{33}H_{34}N_4O_4$ | 551(100) | CI | $CDCl_3 + CF_3CO_2D$/400 MHz | 1.72(2H, m), 1.95–2.01(2H, m), 2.24 (6H, m), 2.48(2H, t), 2.96(2H, m), 3.70 (1H, m), 4.07(2H, t), 4.89(1H, m), 7.0 (2H, d), 7.01((2H, s), 7.15–7.25(4H, m), 7.35(2H, d), 7.48(2H, d), 7.57(2H, d), 8.17(2H, brs). |
| 5371 | $C_{32}H_{32}N_4O_3$ | 521(100) | CI | $CDCl_3$/400 MHz | 1.75–1.80(4H, m), 2.55–2.60(2H, m), 2.75 (2H, t), 2.88(2H, t), 3.50–3.55(2H, m), 3.65(2H, s), 6.95(1H, s), 6.98–7.02 (1H, m), 7.05–7.10(4H, m), 7.15–7.20 (2H, m) 7.38–7.50(5H, m), 7.65(2H, d), 7.85(1H, brs), 8.00(1H, brs), 8.15 (1H, brs). |
| 5379 | $C_{32}H_{32}N_4O_3$.HCl | | | $d_6$-DMSO/400 MHz | 1.60–1.68(2H, m), 1.80–1.88(2H, m), 3.00–3.06(1H, m), 3.15–3.35(6H, m), 3.65–3.75(1H, m), 4.25–4.55(2H, m), 6.80 (2H, brs), 7.18–7.45(7H, m), 7.55–7.65 (4H, m), 7.89(2H, d), 8.57(1H, brs), 10.29(2H, brs), 10.36(1H, brs). |
| 5386 | $C_{35}H_{39}N_5O_4$ | 594(100), 97(50) | ESI | $d_6$-DMSO/400 MHz | 1.81–1.90(2H, m), 2.15(6H, s), 2.35 (2H, t), 2.62–2.70(2H, m), 2.79–2.83 (2H, m), 3.46–3.53(2H, m), 4.02(2H, t), 6.73(1H, s), 6.75(1H, s), 6.73(1H, s), 6.75(1H, s), 6.98(2H, d), 7.02–7.11 (4H, m) 7.50(2H, d), 7.60(2H, d), 7.78 (2H, d), 8.41–8.48(1H, m), 10.22(1H, brs) |
| 5386.2HCl | $C_{35}H_{39}N_5O_4$.2HCl | 594(100), 297(58) | ESI | $d_6$-DMSO/400 MHz | 2.12–2.21(2H, m), 2.72(6H, s), 3.1–3.25 (4H, m), 3.76–3.82(2H, m), 4.12(2H, t), 4.41(2H, brs), 6.78(1H, s), 6.79(1H, s), |

| | | | | | |
|---|---|---|---|---|---|
| | | | | | 7.02(2H, d), 9.05(1H, brs), 10.19 (1H, brs), 10.35(1H, brs). |
| 5388 | $C_{22}H_{25}N_3O_4S$ | | | $d_6$-DMSO/400 MHz | 2.16(6H, s), 2.42(2H, t), 3.55(2H, t), 3.75(2H, t), 4.23(2H, t), 6.43(1H, d), 6.72(1H, s), 6.78(1H, s), 7.22(1H, d), 7.32(1H, m), 7.42(2H, m), 7.53(2H, d). |
| 5388.HCl | $C_{22}H_{25}N_3O_4S\cdot HCl$ | 428(5) | CI | $d_6$-DMSO/400 MHz | 2.72(6H, s), 3.25(2H, t), 3.81(4H, m), 4.32(2H, t), 6.47(1H, d), 6.76(1H, s), 6.81(1H, s), 7.27(1H, d), 7.32(1H, m), 7.42(2H, m), 7.55(2H, d), 10.15 (1H, brs). |
| 5389 | $C_{24}H_{29}N_3O_3S$ | 440(5) | CI | $d_6$-dMSO/400 MHz | 1.28–1.45(6H, m), 1.57(2H, m), 2.12 (6H, s), 2.20(2H, t), 4.13(2H, t), 6.41 (1H, d), 6.75(1H, s), 6.79(1H, s), 7.23 (1H, d), 7.32(1H, m), 7.42(2H, m), 7.55 (2H, d). |
| 5389.HCl | $C_{24}H_{29}N_3O_3S\cdot HCl$ | 440(5) | CI | $d_6$-DMSD/400 MHz | 1.36(2H, m), 1.45(2H, m), 1.66(2H, m), 1.76(2H, m), 2.72(6H, s), 30..(2H, t), 4.13(2H, t), 6.42(1H, d), 6.75(1H, s), 6.80(1H, s), 7.25(1H, d), 7.32(1H, m), 7.41(2H, m), 7.55(2H, d), 10.06 (3H, brs). |
| 5391 | $C_{30}H_{28}N_4O_3$ | 493(100), 489(50) | ESI | $CDCl_3 + CF_3CO_2D$/400 MHz | 3.15–3.25(1H, m), 3.28–3.40(1H, m), 3.48–3.57(1H, m), 3.60–3.68(2H, m), 3.92-4.02(3H, m), 4.33(2H, d), 4.77 (1H, d), 7.11(1H, d), 7.22–7.56(12H, m), 7.85(2H, d). |
| 5391.HCl | $C_{30}H_{28}N_4O_3\cdot HCl$ | 493(100) | ESI | $d_6$-DMSO/400 MHZ | 3.01–3.10(1H, m), 3.38–3.45(4H, m), 3.80–3.85(3H, m), 4.32–4.41(1H, m), 4.61–4.70(1H, m), 6.80(2H, s), 7.18–7.36 (5H, m), 7.41(2H, t), 7.58(2H, d), 7.67 (2H, d), 7.99(2H, d), 9.02(1H, t), 10.29 (1H, brs), 10.39(1H, brs), 10.99 (1H, brs). |
| 5393 | $C_{38}H_{36}N_4O_5$ | | | $d_6$-DMSO/400 MHz | 2.70(6H, m), 2.80(2H, m), 3.55(2H, s), 3.70(6H, s), 6.63(1H, s), 6.65(1H, s), 6.80(1H, s), 6.83(1H, s), 7.22(2H, d), 7.32(1H, m), 7.42(2H, m), 7.55(2H, d), 7.68(4H, d), 7.99(2H, d), 10.15(1H, s), 10.35(2H, br). |
| 5393.HCl | $C_{38}H_{36}N_4O_5\cdot HCl$ | 629(100) | CI | $d_6$-DMSO/400 MHz | 2.95–3.45(8H, m), 3.75(2x3H, s), 4.25–4.50(2H, m), 6.79(1H, s), 6.80(1H, s), 6.82(1H, s), 6.83(1H, s), 7.30(2H, d), 7.32(1H, m), 7.41(2H, m), 7.55(2H, d), 7.68(2H, d), 7.77(2H, d), 8.01(2H, d), 10.28(2H, s), 10.40(1H, s), 10.80 (1H, brs). |
| 5394 | $C_{31}H_{30}N_4O_3$ | 507(15) | CI | $d_6$-DMSO/400 MHz | 1.75–1.85(2H, m), 2.52–2.57(2H, m), 2.67 (2H, t), 2.84(2H, t), 3.34–3.40(2H, m), 3.57(2H, s), 6.75(1H, s), 6.80(1H, s), 7.05–7.10(4H, m), 7.30–7.55(7H, m), 7.84 (2H, d), 8.57(1H, brt), 10.25(2H, brs). |
| 5394.HCl | $C_{31}H_{30}N_4O_3\cdot HCl$ | | | $d_6$-DMSO/400 MHz | 2.02–2.10(2H, m), 2.95–3.01(1H, m), 3.18–3.43(6H, m), 3.65–3.70(1H, m), 4.23–4.53(2H, m), 6.79(1H, s), 6.81 (1H, s), 7.20–7.45(7H, m) 7.55(2H, d), 7.65(2H, d), 7.90(2H, d), 8.70(1H, t), 10.25(1H, s), 10.35(1H, s), 10.60 (1H, brs). |
| 5397 | $C_{37}H_{43}N_5O_4$ | 622(80) | CI | $CDCl_3$/400 MHz | 1.75–1.83(4H, m), 1.95–2.00(2H, m), 2.25 (6H, s), 2.45(2H, t), 2.58–2.61 (2H, m), 2.75(2H, t), 2.85–2.90(2H, m), 3.47–3.52 (2H, m), 3.62(2H, s), 4.05(2H, t), 6.90 (1H, s), 6.95–7.20(10H, m), 7.35(2H, d), 7.65(1H, d), 7.83(1H, brs), 8.15 (1H, brs). |
| 5397.2HCl | $C_{37}H_{43}N_5O_4\cdot 2HCl$ | | | $d_6$-DMSO/400 MHz | 1.60–1.65(2H, m), 1.82–1.90(2H, m), 2.12–2.20(2H, m), 2.79(6H, d), 3.00–3.15 (1H, m), 3.25–3.35(8H, m), 3.65–3.75 (1H, m), 4.13(2H, t), 4.25–4.55(2H, m), 6.75(1H, s), 6.78(1H, s), 7.00(2H, d), 8.60(1H, brt), 10.20(1H, brs), 10.30 (1H, brs). |
| 5402 | $C_{38}H_{35}N_5O_7$ | | | $d_6$-DMSO/400 MHz | 2.70(6H, m), 2.80(2H, m), 3.55(2H, s), 3.70(6H, s), 6.61(1H, s), 6.63(1H, s), 6.80(1H, s), 6.82(1H, s), 7.22(2H, d), 7.68(4H, d), 7.82(2H, d), 7.98(2H, d), 8.22(2H, d), 10.15(1H, s), 10.55 (1H, brs). |

-continued

| | | | | | |
|---|---|---|---|---|---|
| 5402.HCl | C₃₈H₃₅N₅O₇.HCl | 674(80) | ESI | d₆-DMSO/400 MHz | 3.00–3.50(8H, m), 3.73(2x3H, s), 4.25 (2H, m), 6.75(1H, s), 6.79(1H, s), 6.86 (1H, s), 6.88(1H, s), 7.29(2H, d), 7.69 (2H, d), 7.77(4H, m), 8.00(2H, d), 8.25 (2H, d), 10.25(1H, s), 10.55(1H, brs), 10.70(1H, brs). |
| 5376 | C₃₃H₃₄N₄O₄.HCl | 551(100) | ESI | d₆-DMSO/400 MHz | 2.11–2.20(2H, m), 2.78(6H, s), 2.83–2.82 (2H, m), 3.20(2H, m), 3.62(2H, brs), 4.09 (2H, t), 4.75(2H, brs), 6.77(1H, s), 6.79 (1H, s), 7.00(2H, d), 7.19(4H, brs), 7.50 (2H, d), 7.55(2H, d), 7.60(2H, d), 10.19 (1H, brs), 10.32(1H, brs), 10.55 (1H, brs). |
| 5299 | C₂₁H₂₄N₄O₂S | | | d₆-DMSO/400 MHz | 2.18(6H, s), 2.47(2H, t), 3.01(3H, s), 3.40(2H, d), 5.98(1H, d), 6.71(1H, s), 6.85(1H, s), 7.26(1H, d), 7.31(1H, m), 7.41(2H, m), 7.52(2H, d), 9.85(1H, brs). |
| 1912 | C₂₃H₂₄N₄O₃ | 404(55) | EI | d₆-DMSO/400 MHz | 2.25(6H, s), 2.93(2H, s), 4.30(2H, d), 6.74(1H, s), 6.76(1H, s), 7.28–7.55 (9H, m), 8.25(1H, t), 10.20(2H, brs). |

| | Mol. Formula | Mass spec | ¹H nmr | | Microanalysis | |
|---|---|---|---|---|---|---|
| No. | (M. Wt) | m/z, mass intensity (mode) | Solvent δ all 400 MHz | | Calc | Found |
| 1927 | C₁₆H₁₄N₄O₂ 294 | 291, 30%; 295, MH⁺ 100% (DCI, NH₃) | CDCl₃ + TFA 2.45(3H, s), 6.85 (1H, s), 7.38(1H, s), 7.48 (5H, m), 8.95(1H, s). | | | |
| 1926 | C₁₅H₁₂N₄O₂ 280 | 281 MH⁺ 100% (DCI, NH₃) | CDCl₃ + TFA 7.20(1H, s), 7.45 (8H, m). | | | |
| 1545 | C₂₁H₁₇N₃O₃ 359 | 192, 20%; 292, 10%, MH⁺ 360 (DCI NH₃) | CDCl₃ + CF₃CO₂D 7.82(1H, d), 7.75(1H, d), 7.65(1H,), 7.48(3H, m), 7.35(2H, m), 7.25(1H, s), 7.06(2H, d), 3.98(3H, s). | | | |
| 1542 | C₁₆H₁₀N₂O₃Cl₂ 348 | 349, 351, 353, 100%; 366, 368, 370, 50%; 313, 39%. (DCI NH₃) | CDCl₃/TFA 6.72(1H, s), 7.18(2H, 2xs), 7.34(1H, t), 7.43(2H, d), 7.59(1H, s). | | | |
| 1509 | C₂₀H₁₅N₃O₂ | 347 MNH₄⁺, 1%; 330 MH⁺, 100% (DCI NH₃) | CDCl₃/TFA 7.22–7.40(3H, m), 7.40–7.52(6H, m), 7.60(1H, s), 7.78 (1H, d, J=7Hz), 7.81(1H, s), 8.10 (1H, s). | | | |
| 1507 | C₂₂H₂₃N₃O₅ 407 | 310, 100%; 336, 20%; 351, 20%; MH⁺ 410, 5% MNH₄⁺, 427, 2% (DCI NH₃) | CDCl₃ + CF₃CO₂D 7.65(1H, s), 7.48(1H, brs), 7.42(2H, d), 7.22 (1H, s), 7.00(2H, d), 6.72(1H, brd), 6.39(1H, brd), 3.90(3H, s), 1.65 (9H, s). | C H N | 64.54 5.66 10.26 | 64.45 5.61 10.46 | 64.39 5.62 10.43 |
| 1506 | C₂₆H₂₅N₃O₅ 459 | 360, 100%; MH⁺ 460, MNH₄⁺ 477, 2% (DCI NH₃) | CDCl₃ + CF₃CO₂D 8.27(1H, d) 8.05(1H, s) 7.70(1H, d), 7.47(3H, m), 7.38(2H, pt), 7.25(1H, s), 7.05(2H, d), 3.90(3H, s), 1.65(9H, s). | C H N | 67.96 5.48 9.14 | 67.54 5.35 9.21 | 67.63 5.30 9.22 |
| 1476 | C₁₇H₁₄N₂O₄ 310 | 279, 15%; MH⁺, 311; MNH₄⁺, 328, 2% (DCI NH₃) | CDCl₃ + CF₃CO₂D 7.85(1H, s), 7.60(1H, brs), 7.42(2H, d), | C H N | 65.80 4.55 9.03 | 65.87 4.44 9.03 | 65.68 4.54 8.98 |

-continued

| | | | | | | | |
|---|---|---|---|---|---|---|---|
| | | | 7.21(1H, s), 7.08(1H, s), 7.02(2H, d), 6.72(1H, brs), 3.90(3H, s). | | | | |
| 1474 | $C_{17}H_{14}N_2O_3$ 326 | 279, 10%; MH+, 327 (DCI NH$_3$) | CDCl$_3$ + CF$_3$CO$_2$D 7.60(1H, d), 7.45(3H, m), 7.35(1H, s), 7.23(2H, m), 7.05(2H, d), 3.90(3H, s). | C H N | 62.56 4.32 8.58 | 62.41 4.41 8.57 | 62.39 4.46 8.55 |
| 1950 | $C_{25}H_{27}N_3O_4$ 433 | MH+ (100%) 434 CI/NH$_3$ | CDCl$_3$ CF$_3$CO$_2$D 400 MHZ 7.50–7.42(m, 5H), 7.25–7.15(m, 4H), 7.00(d, 1H), 6.96(d, 1H), 6.90(d, 1H), 4.41(t, 2H), 3.90(2, 3H), 3.67(t, 2H), 3.12(s, 6H). | C H N | 69.57 6.28 9.69 | 68.98 6.25 9.59 | 69.06 6.25 9.60 |
| 1718 | $C_{21}H_{17}N_3O_3$ 359 | MH$^+$ 360, 100% (DCI NH$_3$) | DMSO 11.4(1H, s), 10.08(1H, s), 9.82(1H, s), 7.55(3H, m), 7.39(1H, d), 7.18(1H, t), 7.01(4H, m) 6.85(1H, s), 6.78(1H, s), 3.80(3H, s). | | | | |
| 1693 | $C_{22}H_{19}N_3O_5S$ 437 | 360, 85%; 402, 25%, MH$^+$438 (DCI NH$_3$) | 7.98(1H, d), 7.88(1H, s), 7.75(1H, d), 7.45(5H, m), 7.35(1H, s), 7.02(2H, d), 3.90(3H, s), 3.30(2.33H, s). | | | | |
| 1618 | $C_{23}H_{21}N_3O_4S$ 435 | 436, 100%; 336, 82% | CDCl$_3$ TFA 1.75(9H, s), 7.22–7.28(overlapping solvent & sample signals), 7.36–7.50(6H, overlapping signals), 7.61(2H, overlapping signals), 8.10(1H, s). | | | | |
| 1560 | $C_{25}H_{21}N_3O_4Cl_2$ 497 | 498/500/502 (100/69/15)% 398/400/402 (49/31/7)% | DMSO-D6 1.68(9H, s), 6.66(1H, s), 6.92(1H, s), 7.30–7.44(3H, c), 7.49(2H, d), 7.68(1H, d), 8.08(1H, d), 8.17(1H, s). | | | | |
| 1470 | $C_{21}H_{21}N_3O_4$ | 397, MNH$_4$, 4%: 380, MH$^+$, 13%, 280, 100% (DCI NH$_3$) | CDCl$_3$ 1.64(9H, s), 6.33 (1H, br.s), 6.57(1H, br.s), 7.00(1H, s), 7.35–7.50(7H, m), 8.10(1H, br.s), 8.18(1H, br.s) | | | | |
| 1471 | $C_{25}H_{23}N_3O_4$ | 447, MNH$_4^+$, 17%; 430, MH$^+$, 100%; 330, 82% | CDCl$_3$ 1.72(9H, s), 7.07 (1H, s), 7.14(1H, s), 7.30–7.50(7H, m), 7.66(1H, d, J=7Hz), 7.84(1H, s), 8.03(1H, br.s), 8.18(2H, m) | | | | |
| 1729 | $C_{23}H_{19}N_3O_5$ | 435, MNH$_4^+$, 23%; 418, MH$^+$, 100% (DCI NH$_3$) | CDCl$_3$ 3.09(4H, s), 3.92(3H, s), | | | | |

-continued

| | | | | | | | |
|---|---|---|---|---|---|---|---|
| | | | 7.07(2H, d, J=7Hz), 7.28(1H, s), 7.30(1H, s), 7.39(2H, d, J=6Hz), 7.45(2H, d, J=7Hz), 7.60(2H, d, J=6Hz) | | | | |
| 1647 | C$_{23}$H$_{21}$N$_3$O$_3$ 387 | 405, M$^+$NH$_4$, 7%; 388, M$^+$H, 100%; 317, 43%; 459, 29% DCI NH$_3$ | CDCl$_3$ 1.84–2.00(4H, m), 3.13(2H, t), 3.64 (2H, t), 6.98(1H, s), 7.03 (1H, s), 7.32–7.50(9H, m), 8.10(1H, brs), 8.32(1H, brs) | | | | |
| 1845 | C$_{21}$H$_{17}$N$_3$O$_5$ 391 | 409, M$^+$NH$_4$, 35%; 392, MH$^{+,}$ 100% (DCI NH$_3$) | CDCl$_3$ + TFA 2.35(3H, s, Ac), 6.05(2H, s, OCH$_2$O), 6.85–7.60(9H, m) | C H N | 64.45 4.38 10.74 | 63.99 4.42 10.99 | 63.94 4.37 11.01 |
| 1809 | C$_{20}$H$_{16}$N$_2$O$_5$ 364 | 382, M$^+$ + NH$_4$, 5%; 365, MH$^+$, 100% (DCI NH$_3$) | CDCl$_3$ + TFA 3.85(3H, s, OMe), 6.05(2H, s, OCH$_2$O), 6.90–7.45(9H, m) | C H N | 65.93 4.43 7.69 | 65.85 4.38 7.60 | 65.96 4.37 7.65 |
| 1808 | C$_{19}$H$_{14}$N$_2$O$_4$ 334 | 335, M$^+$+1, 100% | CDCl$_3$ + TFA 6.05(2H, s, OCH$_2$O), 6.90–7.50(10H, m) | C H N | 68.26 4.22 8.38 | 68.07 4.15 8.35 | 68.00 4.17 8.35 |
| 1929 | C$_{22}$H$_{18}$N$_4$O$_2$ 370 | MH$^+$, 371 (DCI NH$_3$) | CDCl$_3$ + TFA 5.45(2H, s), 7.18(1H, s), 7.26(1H, s), 7.30(1H, s), 7.45(10H, m), 8.88(1H, s) | | | | |
| 1930 | | MH$^+$, 357, 100% (DCI NH$_3$) | CDCl$_3$ + TFA 7.27(1H, s), 7.30(1H, s), 7.50(5H, m), 7.65(5H, m), 7.75(1H, t), 9.10(1H, s). | | | | |
| 1975 | C$_{27}$H$_{29}$N$_5$O$_3$ | 236, 25%; 257, 100%; 376, 20%; MH$^+$, 472, 20% DCI NH$_3$ | CDCl$_3$ + TFA 2.35(2H, m), 3.01(6H, s), 3.45(2H, t), 4.18(2H, t), 5.40(2H, s), 6.95(2H, d), 7.20(1H, m), 7.25(1H, s), 7.40(3H, m), 7.50(3H, m). | | | | |
| 1976 | C$_{26}$H$_{27}$N$_5$O$_3$ 457 | 230, 100%; 247, 60%; MH$^+$, 458, 90%. DCI NH$_3$ | CDCl$_3$ + TFA 2.30(2H, m), 2.05(6H, s), 3.45(2H, t), 4.18(2H, t), 6.98(2H, d), 7.25(2H, d), 7.45(2H, d), 7.55(3H, m), 7.75(3H, m), 9.18(1H, s). | | | | |
| 1982 | C$_{24}$H$_{28}$N$_4$O$_3$.2HCl 404+73 | 405, 100%, MH$^+$ EI$^+$ | D$_2$O 2.98(3H, s), 3.09(6H, s), 3.75(4H, brs), 4.50(2H, s), 7.09(1H, s), 7.13(1H, s), 7.52–7.68(5H, c), 7.67–7.77 (4H, overlapping signals). | | | | |
| 1983 | C$_{26}$H$_{30}$N$_4$O$_2$ | 431, 25%, MH$^+$; 332, 30%; 303, 18%; 84, 92%: 118, 100%. EI$^+$ | DMSO-D6 1.53(2H, m), 1.71(2H, d), 1.83(2H, t), 2.12(3H, s), 2.14(3H, s), 2.35(1H, m), | | | | |

-continued

| | | | | | | | |
|---|---|---|---|---|---|---|---|
| 1886 | $C_{29}H_{21}N_3O_7$ | | 2.80(2H, d), 3.57(2H, s), 6.78(2H, overlapping signals), 7.34(3H, overlapping signals), 7.43(2H, t), 7.50(2H, d), 7.57(2H, d). $CDCl_3$/TFA 3.90(3H, s), 4.79(2H, s), 7.01(2H, d, J=8Hz), 7.21(1H, s), 7.24(1H, s), 7.27(2H, d, J=8Hz), 7.41(2H, d, J=8Hz), 7.47(2H, d, J=8Hz), 7.82(2H, m), 7.97(2H, m). | | | | |
| 1657 | $C_{20}H_{19}N_3O_3$ 349 | $MH^+$, 350, 12%; $M^+$, 349, 13%; 333, 100%. CI $NH_3$ | $CDCl_3$/TFA 3.92(3H, s), 4.32 (2H, s), 7.05(2H, d), 7.24 (2H, d), 7.45(2H, d), 7.52 (4H, s). | | | | |
| 1891 | $C_{23}H_{24}N_2O_4$ 392 | 392, $M^+$, 25%; 347, $M^+$-$OCH_2CH_3$, 100% EI | DMSO 1.15(6H, t, J=6Hz, $CH_3$), 3.45–3.60 (4H, m, $\underline{CH_2}CH_3$), 5.50(1H, s, $O_2CH$), 6.75(2H, s), 7.28–7.55(9H, m,Ar), 10.25(2H, br.s, NH) | C H N | 70.39 6.16 7.14 | 70.31 6.16 7.03 | 70.03 6.16 7.09 |
| 1912 | $C_{23}H_{24}N_4O_3$ 404 | 404, $M^+$, 55%; 303, $M^+$-$NHC(O)CH_2NMe_2$, 30%: EI | DMSO 2.25(6H, s, 2xMe), 2.95(2H, s), 4.30(2H, d, J=6Hz), 6.74(1H, s), 6.76 (1H, s), 7.28–7.55(9H, m), 8.24–8.27(1H, br.m, NH), 10.20(2H, br.s, 2xNH) | | | | |
| 1676 | $C_{22}H_{19}O_3N_3$ 373 | $MH^+$, 100%, 374 ($DCI/NH_3$) | $CDCl_3$, $CF_3CO_2D$ 7.65(2H, d), 7.58 (2H, d), 7.48(2H, d), 7.41–7.35(4H, m), 7.24(1H, s), 7.12–7.07(2H, m), 2.36+2.23(3H, s, rotamers). | | | | |
| 1959 | $C_{25}H_{28}N_3O_4Cl$ 469/471 | $CI/NH_3$ | $d_6$-DMSO 400 MHz 10.85(1H, s), 10.10(1H, brs), 10.02(1H, s), 7.6–7.30(7H, m), 7.10(2H, m), 6.85(1H, d), 6.80(1H, s), 6.58(1H, d), 4.36(2H, t), 3.87(3H, s), 3.50(2H, t), 2.88(6H, s). | | | | |
| 1921 | $C_{22}H_{21}N_3O_2$ 359 | $MH^+$, 100%, 360 $CI/NH_3$ | $CDCl_3$ + $CF_3CO_2D$ 7.81(2H, d), 7.52(2H, d), 7.40–7.50(6H, m), 7.24(1H, s), 6.98(1H, d), 6.96(1H, d), 3.33(6H, s), | C H N | 73.52 5.89 11.69 | 73.24 5.82 11.50 | 73.11 5.77 11.52 |
| 1922 | $C_{26}H_{20}N_2O_2$ 392 | $MH^+$, 393, 100%: $MNH^+$, 410, 10% $CI/NH_3$ | $d_6$-DMSO 11.15(1H, brs), 10.00(1H, brs), 7.66(1H, d), 7.51–7.30(13H, m), | | | | |

-continued

| | | | | | | | |
|---|---|---|---|---|---|---|---|
| | | | 7.20(2H, m), | | | | |
| | | | 6.78(1H, s), | | | | |
| | | | 6.83(1H, d). | | | | |
| 1923 | $C_{20}H_{15}N_3O_4$ | MH+, 362, 100% | $CDCl_3$ $CF_3CO_2D$ | C | 66.48 | 66.61 | 66.54 |
| | 361 | (DCI $NH_3$) | 8.25(2H, d), | H | 4.18 | 4.23 | 4.26 |
| | | | 7.83(2H, d), | N | 11.63 | 11.40 | 11.48 |
| | | | 7.63(1H, dd), | | | | |
| | | | 7.55–7.45(5H, m), | | | | |
| | | | 7.35(1H, s), | | | | |
| | | | 7.12(1H, d), | | | | |
| | | | 7.08(1H, d). | | | | |
| 1672 | $C_{20}H_{23}N_3O_3$ | MH+, 354, 100%; MNH+, 371, | $CDCl_3$ $CF_3CO_2D$ | | | | |
| | 353 | 10%; 271, 10%; 260, 10% | 7.59(2H, d), | | | | |
| | | (DCI $NH_3$) | 7.45(2H, d), | | | | |
| | | | 7.18(1H, s), | | | | |
| | | | 6.29(1H, d), | | | | |
| | | | 2.55–2.47(1H, m), | | | | |
| | | | 2.36–2.22 | | | | |
| | | | (3H, s, rotamers), | | | | |
| | | | 1.82–1.70(5H, s), | | | | |
| | | | 1.51–1.40(2H, m), | | | | |
| | | | 1.32–1.20(3H, m). | | | | |
| 1884 | $C_{18}H_{20}N_2O_2$ | MH+, 297, 100%; MNH+, 315, | $CDCl_3$ $CF_3CO_2D$ | | | | |
| | 296 | 10% | 7.48–7.38(5H, m), | | | | |
| | | (DCI $NH_3$) | 7.21(1H, s), | | | | |
| | | | 6.26(1H, d), | | | | |
| | | | 2.48(1H, m), | | | | |
| | | | 1.83–1.70(1H, m), | | | | |
| | | | 1.35(2H, m), | | | | |
| | | | 1.30–1.19(3H, m). | | | | |
| 1570 | $C_{17}H_{14}N_2O_2S$ | 311, M+H, 100% | $CDCl_3$ | C | 65.79 | 65.24 | 65.20 |
| | 310 | DCI-$NH_3$ | 4.13(3H, s), | H | 4.55 | 4.53 | 4.49 |
| | | | 6.59(1H, s), | N | 9.03 | 8.73 | 8.79 |
| | | | 7.10(1H, m), | | | | |
| | | | 7.30–7.60(8H, m), | | | | |
| | | | 8.09(1H, brs). | | | | |

We claim:
1. A compound selected from
(3Z,6Z)-3-Benzylidene-6-(4-imidazolyl)methylene-2,5-piperazinedione;
(3Z,6Z)-3-Benzylidene-6-(4-(1-imidazolyl)benzylidene)-2,5-piperazinedione;
(3Z,6Z)-3-Benzylidene-6-(4-(1-imidazolylmethyl)benzylidene)-2,5-piperazinedione;
(3Z,6Z)-3-Benzylidene-6-(4-(2-dimethylaminoethoxy)-3-methoxybenzylidene)-2,5-piperazinedione hydrochloride;
(3Z,6Z)-3-Benzylidene-6-(4-(5-methylimidazolyl))methylene-2,5-piperazinedione;
(3Z,6Z)-3-Benzylidene-6-(4-dimethylaminocinnamylidene)-2,5-piperazinedione;
(3Z,6Z)-3-(4-(3-Dimethylaminopropoxy)benzylidene)-6-(4-(1-imidazolyl)benzylidene-2,5-piperazinedione;
(3Z,6Z)-3-Benzylidene-6-(4-(2-imidazolylethoxy)benzylidene)-2,5-piperazinedione;
(3Z,6Z)-3-Benzylidene-6-(4-nitrocinnamylidene-2,5-piperazinedione;
(3Z,6Z)-3-(4-Aminomethylbenzylidene)-6-(4-methoxybenzylidene)-2,5-piperazinedione;
(3Z,6Z)-3-(1-methanesulfonyl-3-indolyl)methylene-6-(4-methoxybenzylidene)-2,5-piperazinedione;
(3Z,6Z)-3-(4-Methoxybenzylidene)-6-(4-phthalimidoacetoxybenzylidene)-2,5-piperazinedione;
(3Z,6Z)-3-Benzylidene-6-(γ-phenylcinnamylidene)-2,5-piperazinedione;
(3Z,6Z)-3-(1-tert-butoxycarbonyl-3-indolyl)methylene-6-(2-thenylidene-2,5-piperazinedione;
(3Z,6Z)-3-(2,6-Dichlorobenzylidene)-6-(1-tert-butoxycarbonyl-3-indolyl)methylene-2,5-piperazinedione;
(3Z,6Z)-3-Benzylidene-6-(4-(2-dimethylaminoethoxy)-3-methoxycinnamylidene)-2,5-piperazinedione;
(3Z,6Z)-3-(4-(3-Dimethylaminopropoxy)benzylidene)-6-(4-(1-imidazolylmethyl)benzylidene)-2,5-piperazinedione;
(3Z,6Z)-3-Benzylidene-6-(4-N-methyl-N-(4-(N-methylpiperidinyl))aminomethylbenzylidene-2,5-piperazinedione;
((3Z,6Z)-3-Benzylidene-6-(3-indolylmethylene)-2,5-piperazinedione;
(3Z,6Z)-3-(2,6-Dichlorobenzylidene)-6-(3-furylmethylene)-2,5-piperazinedione;
(3Z,6Z)-3-(3-Indolylmethylene)-6-(4-methoxybenzylidene)-2,5-piperazinedione;
(3Z,6Z)-3-(2,6-Dichlorobenzylidene)-6-(3-(1-tertbutoxycarbonyl)indolyl)methylene- 2,5-piperazinedione;
(3Z,6Z,-3-(4-Methoxybenzylidene)-6-(2-(1-tertbutoxycarbonyl)pyrrolyl)methylene-2,5-piperazinedione;
(3Z,3Z)-3-(4-Methoxybenzylidene)-6-(3-(1-tert-butoxyarbonyl)indolyl)methylene-2,5-piperazinedione;
(3Z,6Z)-3-Benzylidene-6-(3-(1-tert-butoxycarbonyl)indolyl)methylene-2,5-piperazinedione;
(3Z,6Z)-3-(4-Methoxybenzylidene)-6-(2-thienyl-methylene)-2,5-piperazinedione;
(3Z,6Z)-(4-Methoxybenzylidene)-6-(3-furylmethylene)-2,5-piperazinedione;
(3Z,6Z)-3-(Acetamidobenzylidene)-6-cyclohexylmethylene-2,5-piperazinedione;
(3Z,6Z)-3-(4-Acetamidobenzylidene)-6-cinnamylidene-2,5-piperazinedione;
(3Z,6Z)-3-Benzylidene-6-(diethoxymethylbenzylidene)-2,5-piperazinedione;

(3Z,6Z)-3-Benzylidene-6-(4-(N-methyl-N-(2-dimethylaminoethyl)aminomethylbenzylidene-2,5-piperazinedione hydrochloride;
(3Z,6Z)-3-Benzylidene-6-cyclohexylmethylene-2,5-piperazinedione;
(3Z,6Z)-3-(4-Acetamidobenzylidene)-6-(3,4-methylenedioxybenzylidene)-2,5-piperazinedione;
(3Z,6Z)-3-(2-Indolylmethylene)-6-(4-methoxy-benzylidene)-2,5-piperazinedione;
(3Z,6Z)-3-Benzylidene-6-(3,4-methylenedioxy-benzylidene)-2,5-piperazinedione;
(3Z,6Z)-3-(4-Methoxybenzylidene)-6-(3,4-methylenedioxybenzylidene)-2,5-piperazinedione;
(3Z,6Z)-3-Benzylidene-6-(2-(1-tertbutoxycarbonyl)pyrrolyl)methylene-2,5-piperazinedione;
(3Z,6Z)-3-(4-Dimethylaminomethylbenzylidene)-6-(4-(3-dimethylaminopropoxy)benzylidene-2,5-piperazinedione;
(3Z,6Z)-3-(4-(3-Dimethylaminopropoxy)benzylidene)-6-(4-(1-imidazolyl)methylbenzylidene)-2,5-piperazinedione;
(3Z,6Z)-3-(4-(3-Dimethylaminopropoxy)benzylidene)-6-(4-(1-imidazolyl)benzylidene;
(2-(4-(3Z,6Z)-6-(4-(3-Dimethylaminopropoxy)benzylidene)-2,5-dioxo-3-piperazinylidene)methylbenzoyl)-1,2,3,4-tetrahydroisoquinoline;
N-(2-(1,2,3,4-Tetrahydro-2-isoquinolyl)ethyl)-4-((3Z,6Z)-6-(4-(3-dimethylaminopropoxy)benzylidene)-2,5-dioxo-3-piperazinylidene)methylbenzamide;
N-(4-(1,2,3,4-Tetrahydro-2-isoquinolyl)butyl)-4-((3Z,6Z)-6-(4-(3-dimethylaminopropoxy)benzylidene)-2,5-dioxo-3-piperazinylidene)methylbenzamide;
(3Z,6Z)-6-(4-(3-Dimethylaminopropoxy)benzylidene-3-(4-pyridylmethylene)-2,5-piperazinedione;
(3Z,6Z)-6-(4-(3-Dimethylaminopropoxy)benzylidene)-3-(3-pyridylmethylene)-2,5-piperazinedione;
(3Z,6Z)-6-(4-(3-Dimethylaminopropoxy)benzylidene)-3-furfurylidene-2,5-piperazinedione;
(3Z,6Z)-6-(4-(3-Dimethylaminopropoxy)benzylidene)-3-(3-Thenylidene)-2,5-piperazinedione;
(3Z,6Z)-6-(4-(3-Dimethylaminopropoxy)benzylidene)-3-(2-Thenylidene)-2,5-piperazinedione;
(3Z,6Z)-6-(4-(3-Dimethylaminopropoxy)benzylidene)-3-(3-Furylmethylene)-2,5-piperazinedione;
(3Z,6Z)-6-(4-(3-Dimethylaminopropoxy)benzylidene)-3-(2-Naphthylmethylene)-2,5-piperazinedione;
(3Z,6Z)-6-(4-(3-Dimethylaminopropoxy)benzylidene)-3-(1-Naphthylmethylene)-2,5-piperazinedione;
(3Z,6Z)-6-Benzylidene-3-(4-(3-dimethylamino-2-hydroxypropoxy)benzylidene)-2,5-piperazinedione;
(3Z,6Z)-6-Benzylidene-3-(4-(2-hydroxy-3-morpholinopropoxy)benzylidene)-2,5-piperazinedione;
(3Z,6Z)-6-Benzylidene-3-(4-(2-hydroxy-3-(1-imidazolyl)propoxy)benzylidene)-2,5-piperazinedione;
(3Z,6Z)-6-Benzylidene-3-(4-(2-hydroxy-3-(4-(2-hydroxyethyl)-1-piperazinyl)propoxy)benzylidene)-2,5-piperazinedione;
(3Z,6Z)-6-(4-(2-Dimethylaminoethoxy)benzylidene)-3-(3-Furylmethylene)-2,5-piperazinedione;
(3Z,6Z)-6-(4-(2-Dimethylaminoethoxy)benzylidene)-3-(3-thenylidene-2,5-piperazinedione;
(3Z,6Z)-6-(4-(2-Dimethylaminoethoxy)benzylidene)-3-(5-methylthio-2-thenylidene)-2,5-piperazinedione;
(3Z,6Z)-6-Benzylidene-3-(4-(2-morpholinoethoxy)benzylidene)-2,5-piperazinedione;
(3Z,6Z)-6-Benzylidene-3-(4-(2-(1-imidazolyl)ethoxy)benzylidene)2,5-piperazinedione;
(3Z,6Z)-6-Benzylidene-3-(4-(2-(1-pyrrolidinyl)ethoxy)benzylidene)2,5-piperazinedione;
(3Z,6Z)-6-(4-(2-Dimethylaminoethoxymethyl)benzylidene)-3-(3-thenylidene)-2,5-piperazinedione;
(3Z,6Z)-6-(4-(2-Dimethylaminoethoxymethyl)benzylidene)-3-(3-furylmethylene)-2,5-piperazinedione;
(3Z,6Z)-6-(4-Dimethylaminoacetamidomethyl benzylidene)-3-(3-thenylidene)-2,5-piperazinedione;
(3Z,6Z)-3-(2-Bromobenzylidene)-6-(4-dimethylaminoacetamidomethylbenzylidene)-2,5-piperazinedione;
(3Z,6Z)-6-(4-Dimethylaminoacetamidomethyl-benzylidene)-3-(3-furylmethylene)-2,5-piperazinedione;
(3Z,6Z)-6-Benzylidene-3-(4-dimethylaminoacetamidomethylbenzylidene)-2,5-piperazinedione;
(3Z,6Z)-6-(4-(2-Dimethylaminoethylthiomethyl)benzylidene)-3-(3-furylmethylene)-2,5-piperazinedione;
(3Z,6Z)-6-(4-(2-Dimethylaminoethylthiomethyl)benzylidene)-3-(3-thenylmethylene)-2,5-piperazinedione;
(3Z,6Z)-6-Benzylidene-3-(4-dimethylaminoacetamidoaminomethylbenzylidene)-2,5-piperazinedione;
(3Z,6Z)-6-Benzylidene-3-(5-(2-dimethylaminoethoxy)-2-thienylmethylene)-2,5-piperazinedione;
(3Z,6Z)-6-Benzylidene-3-(4-(2-dimethylaminoethoxy)-2-thienylmethylene)-2,5-piperazinedione;
(3Z,6Z)-6-Benzylidene-3-(5-(2-dimethylaminoethyl)-2-thienylmethylene)-2,5-piperazinedione;
(3Z,6Z)-6-Benzylidene-3-(5-(2-(2-dimethylaminoethoxy)ethoxy)- 2-thienylmethylene)-2,5-piperazinedione;
(3Z,6Z)-6-Benzylidene-3-(5-(6-dimethylaminohexyloxy)-2-thienylmethylene)-2,5-piperazinedione;
(3Z,6Z)-6-Benzylidene-3-(5-(2-dimethylaminoethyl)methylamino-2-thienylmethylene)-2,5-piperazinedione;
(3Z,6Z)-3-(2,5-Dichloro-3-thenylidene)-6-benzylidene-2,5-piperazinedione;
N-(4-(1,2,3,4-Tetrahydro-2-isoquinolyl)butyl)-4-((3Z,6Z)-6-benzylidene-2,5-dioxo-3-piperazinylidene)methylbenzamide;
N-(2-(1,2,3,4-Tetrahydro-2-isoquinoyl)ethyl)-4-((3Z,6Z)-6-benzylidene-2,5-dioxo-3-piperazinylidene)methylbenzamide;
N-(3-(1,2,3,4-Tetrahydro-2-isoquinolyl)propoyl)-4-((3Z,6Z)-6-benzylidene-2,5-dioxo-3-piperazinylidene)methylbenzamide;
N-(4-(2-(1,2,3,4-Tetrahydro-2-isoquinolyl)ethyl)phenyl-4-((3Z,6Z)-6-benzylidene-2,5-dioxo-3-piperazinylidene)methylbenzamide;
N-(4-(2-(1,2,3,4-Tetrahydro-2-isoquinolyl)ethyl)phenyl)-4-((3Z,6Z)-2,5-dioxo-6-(4-nitrobenzylidene)-3-piperazinylidene)methylbenzamide.

2. A compound which is a piperazine of general formula (A):

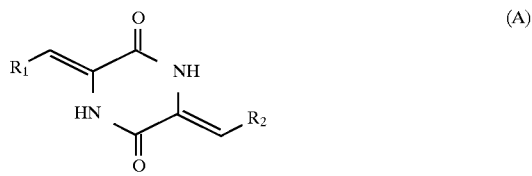

(A)

wherein one of $R_1$ and $R_2$ is a phenyl group which is substituted by X, C(O)X, OC(O)CH$_2$X or C$_2$X wherein X is a heterocyclic ring selected from the group consisting of pyridyl, imidazolyl, furyl, pyrrolyl, pyrrolidinyl, thienyl, piperazinyl, piperidinyl, morpholinyl, quinolyl, isoquinolyl and indolyl, the heteroatoms(s) when nitrogen being optionally substituted by methyl;

and the other of $R_1$ and $R_2$ is a phenyl group optionally substituted by one or more groups selected from halogen nitro, methoxy, $NHC(O)R_{12}$, $CO_2H$, $O(CH_2)_nN(R_{12}R_{13})$, $C_1$–$C_4$ alkyl and $(CH_2)_nC(O)OR_{12}$;

$R_{12}$ and $R_{13}$, which may be the same or different, are hydrogen or $C_1$–$C_6$ alkyl; and n is 0 or an integer having the value 1, 2, 3 or 4; or a pharmaceutically acceptable salt thereof or a pharmaceutically acceptable ester thereof selected from branched and unbranched, saturated and unsaturated $C_1$–$C_6$ alkyl esters.

3. A compound which is a piperazine of general formula (A):

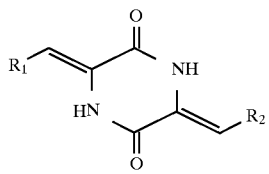

wherein one or both of $R_1$ and $R_2$, which are different, is:
(I) a phenyl group substituted by $CH_2NR_{12}R_{13}$, $OC(O)(CH_2)_nZ$, $CH(OR_{12})(OR_{13})$, $(CH_2)_nNR_{14}C(O)(CH_2)_mNR_{12}R_{13}$, $-CH_2NR_{12}-(CH_2)_nNR_{15}R_{16}$, $O(CH_2)_nCH(OH)(CH_2)_nN(R_{12}R_{13})$;
(II) a group $CH=C(W)V$; or
(III) a cyclohexyl group;
and where appropriate, the other of $R_1$ and $R_2$ is phenyl group optionally substituted by one or more groups independently selected from halogen, nitro, methoxy, $NHC(O)R_{12}$, $CO_2H$, $O(CH_2)_nN(R_{12}R_{13})$, $CH_2Y(CH_2)_nN(R_{12}R_{13})$, $C_1$–$C_4$ alkyl and $(CH_2)_nC(O)OR_{12}$;

Y is O or S;
Z is a $C_3$–$C_6$ cycloalkyl group;
$R_{12}$, $R_{13}$ and $R_{14}$, which may be the same or different, are hydrogen or $C_1$–$C_6$ alkyl;
$R_{15}$ and $R_{16}$, which may be the same or different, are hydrogen or $C_1$–$C_6$ alkyl;
W is hydrogen or a phenyl group;
V is a phenyl group optionally substituted by one or more groups independently selected from nitro, alkoxy and $O(CH_2)_nNR_{12}R_{13}$; and
m and n are each, independently, 0 or an integer having the value 1, 2, 3 or 4; a pharmaceutically acceptable salt thereof or a pharmaceutically acceptable ester thereof selected from branched and unbranched, saturated and unsaturated, $C_1$–$C_6$ alkyl esters.

4. A compound according to claim 3 wherein $R_{12}$ and $R_{13}$, which may be the same or different, are hydrogen or $C_1$–$C_3$ alkyl and n is an integer of value 1 or 2.

5. A compound according to claim 3 wherein one of $R_1$ and $R_2$ is a phenyl group substituted by $CH_2NR_{12}R_{13}$, $OC(O)(CH_2)_nZ$, $CH(OR_{12})(OR_{13})$, $(CH_2)_nNR_{14}C(O)(CH_2)_mNR_{12}R_{13}$; wherein $R_{12}$, $R_{13}$ and $R_{14}$, which may be the same or different, are independently selected from hydrogen and $C_1$–$C_3$ alkyl;
Z is a $C_5$ or $C_6$ cycloalkyl group; and
m and n are, independently, integers having the values 1, 2 or 3.

6. A compound according to claim 3 wherein $R_{12}$, $R_{13}$, $R_{14}$, which may be the same or different, are independently selected from hydrogen and $C_1$–$C_2$ alkyl;

Z is a cyclopentyl group; and
m and n are, independently, integers having the values of 1 or 2.

7. A pharmaceutical composition comprising a pharmaceutically acceptable carrier or diluent and, as an active ingredient, a compound as claimed in claim 1 or 2.

8. A method of treating a patient suffering from a thrombotic disease, thrombotic disorder or haemostatic disorder, the said disease or disorder being associated with elevated levels of PAI-1, which method comprises administering to the patient a therapeutically effective amount of a compound as claimed in claim 7 or 3.

9. A method according to claim 8 wherein the patient is suffering from myocardial infarction, deep vein thrombosis or disseminated intravascular coagulation.

10. A method of treating a patient suffering from a thrombotic disease, thrombotic disorder or haemostatic disorder, the said disease or disorder being associated with elevated levels of PAI-1, which method comprises administering to the patient a therapeutically effective amount of a compound which is a piperazine of formula (A):

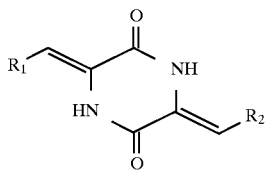

wherein one or both of $R_1$ and $R_2$, which are the same or different, is:
(I) X, of a phenyl group which is substituted by X, C(O)X, $OC(O)CH_2X$, $OCH_2CH_2X$, $CH_2X$, $CONH(CH_2)_nX$, $O(CH_2)_nCH(OH)(CH_2)_nX$ or

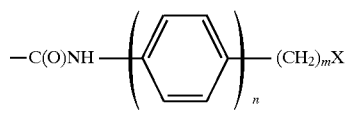

(II) a phenyl group substituted by $CH_2NR_{12}R_{13}$, $OC(O)(CH_2)_nZ$, $CH(OR_{12})(OR_{13})$, $(CH_2)_nNR_{14}C(O)(CH_2)_mNR_{12}R_{13}$ or $O(CH_2)_nCH(OH)(CH_2)_nN(R_{12}R_{13})$; or
(III) a group $CH=C(W)V$; or
(IV) a cyclohexyl group;
and where appropriate, the other of $R_1$ and $R_2$ is a phenyl group optionally substituted by one or more groups independently selected from halogen, nitro, methoxy, $NHC(O)R_{12}$, $CO_2H$, $O(CH_2)_nN(R_{12}R_{13})$ and $CH_2Y(CH_2)_nN(R_{12}R_{13})$;
$R_3$ is $C_1$–$C_4$ alkyl or $(CH_2)_nC(O)OR_{14}$;
X is a five- or six-membered saturated or unsaturated heterocyclic ring selected from the group consisting of pyridyl, imidazolyl, furyl, pyrrolyl, pyrrolidinyl, thienyl, piperazinyl, piperidinyl, morpholinyl, quinolyl, isoquinolyl and indolyl, the heteroatom(s) of the said heterocyclic ring, when nitrogen, being optionally substituted by hydrogen, methyl, oxygen, tertiary-butyloxycarbonyl, $-(CH_2)_nCH_2OH$ or $SO_2Me$; the heterocyclic ring being optionally substituted by halogen, Me, MeS, phenyl, $O(CH_2)_nNR_{12}R_{13}$, $-N(R_{12})(CH_2)_nN(R_{12}R_{13})$, $-(CH_2)_nN(R_{12}R_{13})$ or $-O(CH_2)_nO(CH_2)_nN(R_{12}R_{13})$, or the heterocyclic ring optionally having one or more carbonyl groups;

Y is O or S;

Z is a $C_3$–$C_6$ cycloalkyl group;

$R_{12}$, $R_{13}$ and $R_{14}$, which may be the same or different, are hydrogen or $C_1$–$C_6$ alkyl;

$R_{15}$ and $R_{16}$, which may be the same or different, are hydrogen or $C_1$–$C_6$ alkyl;

W is hydrogen or a phenyl group;

V is a phenyl group optionally substituted by one or more groups independently selected from nitro, alkoxy and $O(CH_2)_n NR_{12} R_{13}$; and m and n are each, independently, 0 or an integer having the value 1, 2, 3 or 4;

a pharmaceutically acceptable salt thereof or a pharmaceutically acceptable ester thereof, selected from the group consisting of branched and unbranched saturated and unsaturated $C_1$–$C_6$ alkyl esters.

11. A method according to claim 10 wherein, in formula (A), one or both of $R_1$ and $R_2$, which may be the same or different, is chosen from X and a phenyl group substituted by X, C(O)X, OC(O)$CH_2$X, $OCH_2CH_2$X, $CH_2$X;

X is a five- or six-membered heterocyclic ring, as defined in claim 1, the heteroatom(s) of the said heterocyclic ring, when nitrogen, being optionally substituted by hydrogen, methyl, oxygen, tertiary-butyloxycarbonyl or $SO_2Me$; the heterocyclic ring being optionally substituted by hydrogen, methyl, phenyl, $O(CH_2)_n N(R_{12}R_{13})$ or optionally having one or more carbonyl groups; and Y, $R_{12}$, $R_{13}$ and n are as defined in claim 1.

12. A method according to claim 10, wherein, in formula (A), $R_{12}$ and $R_{13}$, which may be the same or different, are hydrogen or $C_1$–$C_3$ alkyl and n is an integer of value 1 or 2.

13. A method according to claim 10 wherein, in formula (A), one of $R_1$ and $R_2$ is a phenyl group which is substituted by X, C(O), OC(O)$CH_2$X, $OCH_2CH_2$X, $CH_2$X or which is fused to a group X; wherein X is a heterocyclic ring as defined in claim 10, the heteroatoms(s), when nitrogen, being optionally substituted by methyl.

14. A method according to claim 10 wherein, in formula (A), one of $R_1$ and $R_2$ is a phenyl group substituted by $CH_2NR_{12}R_{13}$, $OC(O)(CH_2)_nZ$, $CH(OR_{12})(OR_{13})$, $(CH_2)_nNR_{14}C(O)(CH_2)_mNR_{12}R_{13}$; wherein $R_{12}$, $R_{13}$ and $R_{14}$, which may be the same or different, are independently selected from hydrogen or $C_1$–$C_3$ alkyl;

Z is a $C_5$ or $C_6$ cycloalkyl group;

and m and n are, independently, integers having the values 1, 2 or 3.

15. A method according to claim 10 wherein, in formula (A), $R_{12}$, $R_{13}$ and $R_{14}$, which may the same or different, are independently selected from hydrogen and $C_1$–$C_2$ alkyl;

Z is a cyclopentyl group; and m and n are, independently, integers having the values of 1 or 2.

16. A method of treating a patient suffering from a thrombotic disease, thrombotic disorder or haemostatic disorder, the said disease or disorder being associated with elevated levels of PAI-1 which method comprises administering to the patient a therapeutically effective amount of a compound selected from (3Z,6Z)-3-Benzylidene-6-(4-imidazolyl)methylene-2,5-piperazinedione;

(3Z,6Z)-3-Benzylidene-6-(4-(1-imidazolyl)benzylidene)-2,5-piperazinedione;

(3Z,6Z)-3-Benzylidene-6-(4-(1-imidazolylmethyl)benzylidene-2,5-piperazinedione;

(3Z,6Z)-3-Benzylidene-6-(4-(2-dimethylaminoethoxy)-3-methoxybenzylidene)-2,5-piperazinedione hydrochloride;

(3Z,6Z)-3-Benzylidene-6-(4-(5-methylimidazolyl))methylene-2,5-piperazinedione;

(3Z,6Z)-3-Benzylidene-6-(4-dimethylamino-cinnamylidene)-2,5-piperazinedione;

(3Z,6Z)-3-(4-(3-Dimethylaminopropoxy)benzylidene)-6-(4-(1-imidazolyl)benzylidene-2,5-piperazinedione;

(3Z,6Z)-3-Benzylidene-6-(4-(2-imidazolylethoxy)benzylidene)-2,5-piperazinedione;

(3Z,6Z)-3-Benzylidene-6-(4-nitrocinnamylidene-2,5-piperazinedione;

(3Z,6Z)-3-(4-Aminomethylbenzylidene)-6-(4-methoxybenzylidene)-2,5-piperazinedione;

(3Z,6Z)-3-(1-methanesulfonyl-3-indolyl)methylene-6-(4-methoxybenzylidene)-2,5-piperazinedione;

(3Z,6Z)-3-(4-Methoxybenzylidene)-6-(4-phthalimidoacetoxybenzylidene)-2,5-piperazinedione;

(3Z,6Z)-3-Benzylidene-6-(γ-phenylcinnamylidene)-2,5-piperazinedione;

(3Z,6Z)-3-(1-tert-butoxycarbonyl-3-indolyl)methylene-6-(2-thenylidene)-2,5-piperazinedione;

(3Z,6Z)-3-(2,6-Dichlorobenzylidene)-6-(1-tert-butoxycarbonyl-3-indolyl)methylene-2,5-piperazinedione;

(3Z,6Z)-3-Benzylidene-6-(4-(2-dimethylaminoethoxy)-3-methoxycinnamylidene-2,5-piperazinedione;

(3Z,6Z)-3-(4-(3-Dimethylaminopropoxy)benzylidene-6-(4-(1-imidazolylmethyl)benzylidene)-2,5-piperazinedione;

(3Z,6Z)-3-Benzylidene-6-(4-N-methyl-N-(4-(N-methylpiperidinyl))aminomethylbenzylidene-2,5-piperazinedione;

((3Z,6Z)-3-Benzylidene-6-(3-indolylmethylene)-2,5-piperazinedione;

(3Z,6Z)-3-(2,6-Dichlorobenzylidene)-6-(3-furylmethylene)-2,5-piperazinedione;

(3Z,6Z)-3-(3-Indolylmethylene)-6-(4-methoxybenzylidene)-2,5-piperazinedione;

(3Z,6Z)-3-(2,6-Dichlorobenzylidene)-6-(3-(1-tertbutoxycarbonyl)indolyl)methylene-2,5-piperazinedione;

(3Z,6Z)-3-(4-Methoxybenzylidene)-6-(2-(1-tertbutoxycarbonyl)pyrrolyl)methylene-2,5-piperazinedione;

(3Z,6Z)-3-(4-Methoxybenzylidene)-6-(3-(1-tertbutoxycarbonyl)indolyl)methylene-2,5-piperazinedione;

(3Z,6Z)-3-Benzylidene-6-(3-(1-tertbutoxycarbonyl)indolyl)methylene-2,5-piperazinedione;

(3Z,6Z)-3-(4-Methoxybenzylidene)-6-(2-thienyl-methylene)-2,5-piperazinedione;

(3Z,6Z)-3-(4-Methoxybenzylidene)-6-(3-furylmethylene)-2,5-piperazinedione;

(3Z,6Z)-3-(Acetamidobenzylidene)-6-cyclohexylmethylene-2,5-piperazinedione;

(3Z,6Z)-3-(4-Acetamidobenzylidene)-6-cinnamylidene-2,5-piperazinedione;

(3Z,6Z)-3-Benzylidene-6-(diethoxymethylbenzylidene)-2,5-piperazinedione;

(3Z,6Z)-3-Benzylidene-6-(4-(N-methyl-N-(2-dimethylaminoethyl)aminomethylbenzylidene-2,5-piperazinedione hydrochloride;

(3Z,6Z)-3-Benzylidene-6-cyclohexylmethylene-2,5-piperazinedione;

(3Z,6Z)-3-(4-Acetamidobenzylidene)-6-(3,4-methylenedioxybenzylidene)-2,5-piperazinedione;

(3Z,6Z)-3-(2-Indolylmethylene)-6-(4-methoxybenzylidene)-2,5-piperazinedione;

(3Z,6Z)-3-Benzylidene-6-(3,4-methylenedioxybenzylidene)-2,5-piperazinedione;

(3Z,6Z)-3-(4-Methoxybenzylidene)-6-(3,4-methylenedioxybenzylidene)-2,5-piperazinedione;

(3Z,6Z)-3-Benzylidene-6-(2-(1-tertbutoxycarbonyl)pyrrolyl)methylene-2,5-piperazinedione;

(3Z,6Z)-3-(4-Dimethylaminomethylbenzylidene)-6-(4-(3-dimethylaminopropoxy)benzylidene-2,5-piperazinedione;

(3Z,6Z)-3-(4-(3-dimethylaminopropoxy)benzylidene)-6-(4-(1-imidazolyl)methylbenzylidene)-2,5-piperazinedione;

(3Z,6Z)-3-(4-(3-Dimethylaminopropoxy)benzylidene)-6-(4-(1-imidazolyl)benzylidene;

(2-(4-((3Z,6Z)-6-(4-(3-Dimethylaminopropoxy)benzylidene)-2,5-dioxo-3-piperazinylidene)methylbenzoyl)-1,2,3,4-tetrahydroisoquinoline;

N-(2-(1,2,3,4-Tetrahydro-2-isoquinolyl)ethyl)-4-((3Z,6Z)-6-(4-(3-dimethylaminopropoxy)benzylidene-2,5-dioxo-3-piperazinylidene)methylbenzamide;

N-(4-(1,2,3,4-Tetrahydro-2-isoquinolyl)butyl)-4-((3Z,6Z)-6-(4-(3-dimethylaminopropoxy)benzylidene)-2,5-dioxo-3-piperazinylidene)methylbenzamide;

(3Z,6Z)-6-(4-(3-Dimethylaminopropoxy)benzylidene-3-(4-pyridylmethylene)-2,5-piperazinedione;

(3Z,6Z)-6-(4-(3-Dimethylaminopropoxy)benzylidene)-3-(3-pyridylmethylene)-2,5-piperazinedione;

(3Z,6Z)-6-(4-(3-Dimethylaminopropoxy)benzylidene)-3-furfurylidene-2,5-piperazinedione;

(3Z,6Z)-6-(4-(3-Dimethylaminopropoxy)benzylidene)-3-(3-Thenylidene)-2,5-piperazinedione;

(3Z,6Z)-6-(4-(3-Dimethylaminopropoxy)benzylidene)-3-(2-Thenylidene)-2,5-piperazinedione;

(3Z,6Z)-6-(4-(3-Dimethylaminopropoxy)benzylidene)-3-(3-furylmethylene)-2,5-piperazinedione;

(3Z,6Z)-6-(4-(3-Dimethylaminopropoxy)benzylidene)-3-(2-Naphthylmethylene)-2,5-piperazinedione;

(3Z,6Z)-6-(4-(3-Dimethylaminopropoxy)benzylidene)-3-(1-Naphthylmethylene)-2,5-piperazinedione;

(3Z,6Z)-6-Benzylidene-3-(4-(3-dimethylamino-2-hydroxypropoxy)benzylidene)-2,5-piperazinedione;

(3Z,6Z)-6-Benzylidene-3-(4-(2-hydroxy-3-morpholinopropoxy)benzylidene)-2,5-piperazinedione;

(3Z,6Z)-6-Benzylidene-3-(4-(2-hydroxy-3-(1-imidazolyl)propoxy)benzylidene)-2,5-piperazinedione;

(3Z,6Z)-6-Benzylidene-3-(4-(2-hydroxy-3-(4-(2-hydroxyethyl)-1-piperazinyl)propoxy)benzylidene)-2,5-piperazinedione;

(3Z,6Z)-6-(4-(2-Dimethylaminoethoxy)benzylidene)-3-(3-Furylmethylene)-2,5-piperazinedione;

(3Z,6Z)-6-(4-(2-Dimethylaminoethoxy)benzylidene)-3-(3-thenylidene)-2,5-piperazinedione;

(3Z,6Z)-6-(4-(2-Dimethylaminoethoxy)benzylidene)-3-(5-methylthio-2-thenylidene)-2,5-piperazinedione;

(3Z,6Z)-6-Benzylidene-3-(4-(2-morpholinoethoxy)benzylidene)-2,5-piperazinedione;

(3Z,6Z)-6-Benzylidene-3-(4-(2-(1-imidazolyl)ethoxy)benzylidene)-2,5-piperazinedione;

(3Z,6Z)-6-Benzylidene-3-(4-(2-(1-pyrrolidinyl)ethoxy)benzylidene)-2,5-piperazinedione;

(3Z,6Z)-6-(4-(2-Dimethylaminoethoxymethyl)benzylidene)-3-(3-thenylidene)-2,5-piperazinedione;

(3Z,6Z)-6-(4-(2-Dimethylaminoethoxymethyl)benzylidene)-3-(3-furylmethylene)-2,5-piperazinedione;

(3Z,6Z)-6-(4-Dimethylaminoacetamidomethylbenzylidene)-3-(3-thenylidene)-2,5-piperazinedione;

(3Z,6Z)-3-(2-Bromobenzylidene)-6-(4-dimethylaminoacetamidomethylbenzylidene)-2,5-piperazinedione;

(3Z,6Z)-6-(4-Dimethylaminoacetamidomethyl-benzylidene)-3-(3-furylmethylene)-2,5-piperazinedione;

(3Z,6Z)-6-Benzylidene-3-(4-dimethylaminoacetamidomethylbenzylidene)-2,5-piperazinedione;

(3Z,6Z)-6-(4-(2-Dimethylaminoethylthiomethyl)benzylidene)-3-(3-furylmethylene)-2,5-piperazinedione;

(3Z,6Z)-6-(4-(2-Dimethylaminoethylthiomethyl)benzylidene)-3-(3-thenylidene)-2,5-piperazinedione;

(3Z,6Z)-6-Benzylidene-3-(4-dimethylaminoacetamidoaminomethylbenzylidene)-2,5-piperazinedione;

(3Z,6Z)-6-Benzylidene-3-(5-(2-dimethylaminoethoxy)-2-thienylmethylene)-2,5-piperazinedione;

(3Z,6Z)-6-Benzylidene-3-(4-(2-dimethylaminoethoxy)-2-thienylmethylene)-2,5-piperazinedione;

(3Z,6Z)-6-Benzylidene-3-(5-(2-dimethylaminoethyl)-2-thienylmethylene)-2,5-piperazinedione;

(3Z,6Z)-6-Benzylidene-3-(5-(2-(2-dimethylaminoethoxy)ethoxy)-2-thienylmethylene)-2,5-piperazinedione;

(3Z,6Z)-6-Benzylidene-3-(5-(6-dimethylaminohexyloxy)-2-thienylmethylene)-2,5-piperazinedione;

(3Z,6Z)-6-Benzylidene-3-(5-(2-dimethylaminoethyl)methylamino-2-thienylmethylene)-2,5-piperazinedione;

(3Z,6Z)-3-(2,5-Dichloro-3-thenylidene)-6-benzylidene-2,5-piperazinedione;

N-(4-(1,2,3,4-Tetrahydro-2-isoquinolyl)butyl)-4-((3Z,6Z)-6-benzylidene-2,5-dioxo-3-piperazinylidene)methylbenzamide;

N-(2-(1,2,3,4-Tetrahydro-2-isoquinolyl)ethyl)-4-((3Z,6Z)-6-benzylidene-2,5-dioxo-3-piperazinylidene)methylbenzamide;

N-(3-(1,2,3,4-Tetrahydro-2-isoquinolyl)propylpropoyl)-4-((3Z,6Z)-6-benzylidene-2,5-dioxo-3-piperazinylidene)methylbenzamide;

N-(4-(2-(1,2,3,4-Tetrahydro-2-isoquinolyl)ethyl)phenyl-4-((3Z,6Z)-6-benzylidene-2,5-dioxo-3-piperazinylidene)methylbenzamide;

N-(4-(2-(1,2,3,4-Tetrahydro-2-isoquinolyl)ethyl)phenyl)-4-((3Z,6Z)-2,5-dioxo-6-(4-nitrobenzylidene)-3-piperazinylidene)methylbenzamide.

17. A method according to claim 10 wherein the patient is suffering from myocardial infarctions deep vein thrombosis or disseminated intravascular coagulation.

18. A method according to claim 8 or 10 which further comprises the combined administration to the patient of a therapeutically effective amount of tissue plasminogen activator.

* * * * *

UNITED STATES PATENT AND TRADEMARK OFFICE
CERTIFICATE OF CORRECTION

PATENT NO. : 5,891,877
DATED : April 6, 1999
INVENTOR(S) : Brocchini, et al

It is certified that error appears in the above-identified patent and that said Letters Patent is hereby corrected as shown below:

On the title page, under item [73], insert the following:

-- [*] Notice: This patent is subject to a terminal disclaimer. --

Signed and Sealed this

Nineteenth Day of October, 1999

Attest:

Q. TODD DICKINSON

Attesting Officer

Acting Commissioner of Patents and Trademarks